(12) United States Patent
DeAnglis et al.

(10) Patent No.: US 11,957,324 B2
(45) Date of Patent: Apr. 16, 2024

(54) DEVICE AND METHOD FOR PREPARING AND ADMINISTERING ONE-COMPONENT FIBRIN SEALANT

(71) Applicants: Ethicon, Inc., Somerville, NJ (US); Omrix Biopharmaceuticals Ltd., Rehovot (IL)

(72) Inventors: Ashley DeAnglis, Skillman, NJ (US); Yair Pilpel, Rehovot (IL); Yuri Zherdev, Rehovot (IL); Sivan Doron, Moshav Arugot (IL); Lior Erez, Rehovot (IL)

(73) Assignees: Ethicon, Inc., Sommerville, NJ (US); Omrix Biopharmaceuticals, Ltd., Kiryat-Ono (IL)

( * ) Notice: Subject to any disclaimer, the term of this patent is extended or adjusted under 35 U.S.C. 154(b) by 261 days.

(21) Appl. No.: 17/318,740

(22) Filed: May 12, 2021

(65) Prior Publication Data

US 2021/0267581 A1 Sep. 2, 2021

Related U.S. Application Data

(62) Division of application No. 16/412,487, filed on May 15, 2019, now Pat. No. 11,020,100, which is a division of application No. 14/668,341, filed on Mar. 25, 2015, now Pat. No. 10,433,825.

(60) Provisional application No. 61/970,929, filed on Mar. 27, 2014.

(30) Foreign Application Priority Data

Mar. 27, 2014 (IL) .......................................... 231792

(51) Int. Cl.
| | | |
|---|---|---|
| A61M 5/178 | (2006.01) | |
| A61B 17/00 | (2006.01) | |
| A61K 38/36 | (2006.01) | |
| A61K 38/48 | (2006.01) | |
| A61L 15/32 | (2006.01) | |
| A61L 24/10 | (2006.01) | |
| A61M 3/00 | (2006.01) | |

(52) U.S. Cl.
CPC ........ *A61B 17/00491* (2013.01); *A61K 38/36* (2013.01); *A61K 38/363* (2013.01); *A61K 38/4833* (2013.01); *A61L 24/106* (2013.01); *A61M 3/005* (2013.01); *A61M 2202/045* (2013.01); *C12Y 304/21005* (2013.01)

(58) Field of Classification Search
None
See application file for complete search history.

(56) References Cited

U.S. PATENT DOCUMENTS

| | | |
|---|---|---|
| 4,627,879 A | 12/1986 | Rose et al. |
| 4,874,368 A | 10/1989 | Miller et al. |
| 4,978,336 A | 12/1990 | Capozzi |
| 5,104,375 A | 4/1992 | Wolf et al. |
| 5,143,838 A | 9/1992 | Kraus et al. |
| 5,219,328 A | 6/1993 | Morse et al. |
| 5,318,524 A | 6/1994 | Morse et al. |
| 5,478,810 A | 12/1995 | Stueber et al. |
| 5,607,858 A | 3/1997 | Stueber et al. |
| 5,723,579 A | 3/1998 | Buettner et al. |
| 5,750,657 A | 5/1998 | Edwardson et al. |
| 5,792,835 A | 8/1998 | Tse |
| 5,831,005 A | 11/1998 | Zuckerman et al. |
| 5,877,278 A | 3/1999 | Zuckermann et al. |
| 5,977,301 A | 11/1999 | Zuckerman et al. |
| 5,985,315 A | 11/1999 | Patat et al. |
| 6,121,232 A | 9/2000 | Nur et al. |
| 6,121,422 A | 9/2000 | Zimmerman et al. |
| 6,234,994 B1 | 5/2001 | Zinger |
| 6,262,236 B1 | 7/2001 | Edwardson et al. |
| 6,268,483 B1 | 7/2001 | Edwardson et al. |
| 6,500,427 B1 | 12/2002 | Heimburger et al. |
| 6,613,020 B1 | 9/2003 | Holm et al. |
| 6,783,514 B2 | 8/2004 | Tovey et al. |
| 6,908,899 B2 | 6/2005 | Smith |
| 7,125,569 B2 | 10/2006 | Nur et al. |
| 7,208,087 B2 | 4/2007 | Cummings |
| 8,367,802 B2 | 2/2013 | Falus et al. |
| 8,513,380 B2 | 8/2013 | Barker |
| 2005/0080009 A1 | 4/2005 | Metzner et al. |
| 2010/0249044 A1 | 9/2010 | Walker |

(Continued)

FOREIGN PATENT DOCUMENTS

| | | |
|---|---|---|
| EP | 0037393 A1 | 10/1981 |
| EP | 0592242 A1 | 4/1994 |

(Continued)

OTHER PUBLICATIONS

Achyuthan, et al., Gly-Pro-Arg-pro modifies the glutamine residues in the X- and y-chains of fibrinogen: inhibition of transglutaminase cross-linking Biochimica et Biophysica Acta—Protein Stucture and Moleculare Enzymology, Science Direct, Aug. 15, 1986, pp. 261-268, vol. 872 Issue 3.

(Continued)

*Primary Examiner* — Marsha Tsay
(74) *Attorney, Agent, or Firm* — David R. Crichton

(57) ABSTRACT

Provided herein are systems for preparing and delivering fibrin sealant to a surface and methods of use thereof. In one embodiment, the system comprises: a. a quantity of a liquid mixture disposed within a container, the mixture comprising: I. fibrin or II. fibrinogen and Factor II; and b. a resin bed disposed within a vessel, the vessel capable of being in fluid communication with the container, wherein when in fluid communication, passage of the mixture through the vessel results in modification of the concentration of small molecules inhibitor(s) and/or inducer(s) within the mixture, favoring fibrin clot formation.

1 Claim, 8 Drawing Sheets

Specification includes a Sequence Listing.

(56) References Cited

U.S. PATENT DOCUMENTS

| | | |
|---|---|---|
| 2011/0306058 A1 | 12/2011 | Van Dreden et al. |
| 2012/0114682 A1 | 5/2012 | Barker |
| 2013/0149292 A1 | 6/2013 | Chtourou |
| 2015/0174289 A1 | 6/2015 | Pilpel et al. |
| 2015/0272562 A1 | 10/2015 | Deanglis et al. |
| 2018/0000982 A1 | 1/2018 | Pilpel et al. |

FOREIGN PATENT DOCUMENTS

| | | |
|---|---|---|
| EP | 0839498 A1 | 5/1998 |
| EP | 1390485 A1 | 2/2004 |
| WO | 9109641 A1 | 7/1991 |
| WO | 1993/05822 A1 | 4/1993 |
| WO | 9729792 A1 | 8/1997 |
| WO | 9820931 A1 | 5/1998 |
| WO | 98/033533 | 8/1998 |
| WO | 02/095019 | 11/2002 |
| WO | 03028743 A1 | 4/2003 |
| WO | 2007059801 A1 | 5/2007 |
| WO | 2010066869 A2 | 6/2010 |
| WO | 2015097687 A1 | 7/2015 |
| WO | 2015097688 A1 | 7/2015 |
| WO | 2015145416 A1 | 10/2015 |

OTHER PUBLICATIONS

Bertolini, J. et al., Production of Plasma Proteins for the Therapeutic Use, (2013) Wiley Press.

Bio-Rad, Bio-Rad Protein Purification Bio Scale Mini Cartridges, Bio-Rad, 2006, pp. 1-2, Page Number.

Dickneite, et al., A Comparison of fibrin sealants in relation to their in vitro and in vivi properties, Thrombosis Research, Oct. 1, 2003, pp. 73-82, vol. 112, Elsevier Ltd.

GE Healthcare Instructions 52-1308-00 BB PD-10 Desalting Columns Nov. 1, 2007 pp. 1-12 retrieved from https://www.gelifesciences.com/gehcls_images/GELS/RelatedContent/Files/1314723116657/litdoc52130800BB_20110830191706.pdf [retrieved on Jul. 7, 2015].

Hermanson, et al., Immobilized Affinity Ligand Techniques, Academic Press Inc, 1992, pp. 1-45, Page Number.

International Preliminary Report on Patentability re: PCT/IL2014/000063 dated Jun. 28, 2016.

International Preliminary Report on Patentability re: PCT/IL2015/000018 dated Sep. 27, 2016.

International Search Report re: PCT/IL2014/000063 dated Apr. 13, 2015.

International Search Report re: PCT/IL2015/000018 dated Jul. 31, 2015.

Laudano, et al., Synthetic peptide derivatives that bind to fibrinogen and prevent the polymerization of fibrin monomers, Proc Natl Acad Sci., 1978, pp. 3085-3089, vol. 75 Issue 7.

Nguyen, et al., Improving Sh3 domain Ligand selectivity using a non-natural scaffold, Research paper, Jun. 12, 2000, pp. 463-473, vol. 7 Issue 7, Elsevier Ltd.

Raccuia, et al., Comparative efficacy of Topical hemostatic Agents in a Rat Kidney Model, The American Journal of Surgery, 1992, pp. 234-238, vol. 163.

Rogner, M. 'Chapter 2, Size Exclusion Chromatography' Protein Liquid Chromatography Journal of Chromatography Library vol. 61 Elsevier Science (2000) pp. 94-114.

Simon, et al., Peptoids: A modular approach to drug discovery, Proc.Natl. Acad Sci,, Oct. 1992, pp. 9367-9373, vol. 89.

Stabenfeldt, et al., Engineering fibrin polymers through engagement of alternative polymerization mechanisms, Biomaterials, 2012, pp. 535-544, vol. 33.

Stuart and Young (1984), "Solid Phase Peptide Synthesis," Solid Phase Peptide Synthesis, Methods Enzymol., Second Edition, Pierce Chemical Company, 289, Academic Press, Inc., NY (1997).

Tabele, et al., organic Glues or fibrin Glues from pooled plasma: Efficacy, Safety and potential as scaffold Delivery System, J Pharm Pharmaceul Sci., Jan. 5, 2012, pp. 124-140, vol. 15 Issue 1.

SEQUENCE LISTING

```
<160> NUMBER OF SEQ ID NOS: 42

<210> SEQ ID NO 1
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 1

Gly Pro Arg Pro
1

<210> SEQ ID NO 2
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 2

Gly Pro Arg Pro Pro
1               5

<210> SEQ ID NO 3
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 3

Gly Pro Arg Pro Ala
1               5

<210> SEQ ID NO 4
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 4

Gly Pro Arg Pro Ser
1               5
```

```
<210> SEQ ID NO 5
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 5

Gly Pro Arg Pro Lys
1               5

<210> SEQ ID NO 6
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 6

Gly Pro Arg Pro Phe
1               5

<210> SEQ ID NO 7
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 7

Gly Pro Arg Pro Gly
1               5

<210> SEQ ID NO 8
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 8

Gly Pro Arg Pro Trp
1               5

<210> SEQ ID NO 9
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 9

Gly Pro Arg Pro Tyr
1               5

<210> SEQ ID NO 10
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 10

Gly Pro Arg Pro Val
1               5
```

```
<210> SEQ ID NO 11
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 11

Gly Pro Arg Pro Ile
1               5

<210> SEQ ID NO 12
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 12

Gly Pro Arg Pro Asp
1               5

<210> SEQ ID NO 13
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 13

Gly Pro Arg Pro Glu
1               5

<210> SEQ ID NO 14
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 14

Gly Pro Arg Pro Gly
1               5

<210> SEQ ID NO 15
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 15

Gly Pro Arg Pro Ser
1               5

<210> SEQ ID NO 16
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 16

Gly Pro Arg Pro Pro Pro
1               5
```

```
<210> SEQ ID NO 17
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 17

Gly Pro Arg Pro Gly Gly
1               5

<210> SEQ ID NO 18
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 18

Gly Pro Arg Pro Pro Arg
1               5

<210> SEQ ID NO 19
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 19

Gly Pro Arg Pro Arg Pro
1               5

<210> SEQ ID NO 20
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 20

Gly Pro Arg Pro Ala Gly
1               5

<210> SEQ ID NO 21
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 21

Gly Pro Arg Pro Gly Gly
1               5

<210> SEQ ID NO 22
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 22

Gly Lys Arg Pro Gly
1               5
```

```
<210> SEQ ID NO 23
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 23

Gly Lys Arg Val
1

<210> SEQ ID NO 24
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 24

Gly His Arg Pro
1

<210> SEQ ID NO 25
<211> LENGTH: 7
<212> TYPE: PRT
<213> ORGANISM: ARTIFICIAL
<220> FEATURE:
<223> OTHER INFORMATION: Synthetic peptide

<400> SEQUENCE: 25

Gly Pro Arg Pro Ala Ala Cys
1               5

<210> SEQ ID NO 26
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 26

Gly Pro Arg Pro Phe Pro Ala Cys
1               5

<210> SEQ ID NO 27
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 27

Gly Pro Arg Pro Pro Glu Arg Cys
1               5

<210> SEQ ID NO 28
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 28

Gly Pro Arg Val Val Glu Arg Cys
1               5
```

```
<210> SEQ ID NO 29
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 29

Gly Pro Arg Val Val Ala Ala Cys
1               5

<210> SEQ ID NO 30
<211> LENGTH: 7
<212> TYPE: PRT
<213> ORGANISM: ARTIFICIAL
<220> FEATURE:
<223> OTHER INFORMATION: Synthetic peptide

<400> SEQUENCE: 30

Gly Pro Ser Pro Ala Ala Cys
1               5

<210> SEQ ID NO 31
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 31

Gly Pro Arg Pro Ala Ala
1               5

<210> SEQ ID NO 32
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Gly Pro Arg Pro Xaa
1               5

<210> SEQ ID NO 33
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Gly Pro Arg Val Xaa
1               5

<210> SEQ ID NO 34
<211> LENGTH: 6
<212> TYPE: PRT
<213> ORGANISM: ARTIFICIAL
<220> FEATURE:
<223> OTHER INFORMATION: Synthetic peptide
```

```
<220> FEATURE:
<221> NAME/KEY: misc_feature
<222> LOCATION: (5)..(6)
<223> OTHER INFORMATION: Xaa can be any naturally occurring amino acid

<400> SEQUENCE: 34

Gly Pro Arg Pro Xaa Xaa
1               5

<210> SEQ ID NO 35
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 35

Gly Pro Arg Val Xaa Xaa
1               5

<210> SEQ ID NO 36
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid

<400> SEQUENCE: 36

Gly Pro Arg Pro Xaa Xaa Xaa
1               5

<210> SEQ ID NO 37
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid

<400> SEQUENCE: 37

Gly Pro Arg Val Xaa Xaa Xaa
1               5

<210> SEQ ID NO 38
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(8)
<223> OTHER INFORMATION: Xaa can be any naturally occurring amino acid

<400> SEQUENCE: 38

Gly Pro Arg Pro Xaa Xaa Xaa Xaa
1               5
```

```
<210> SEQ ID NO 39
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(8)
<223> OTHER INFORMATION: Xaa can be any naturally occurring amino acid

<400> SEQUENCE: 39

Gly Pro Arg Val Xaa Xaa Xaa Xaa
1               5

<210> SEQ ID NO 40
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 40

Gly Pro Arg Xaa Xaa Xaa
1               5

<210> SEQ ID NO 41
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 41

Gly Pro Arg Pro Phe Xaa Xaa
1               5

<210> SEQ ID NO 42
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 42

Gly Pro Arg Val Phe Xaa Xaa
1               5
```

DEVICE AND METHOD FOR PREPARING AND ADMINISTERING ONE-COMPONENT FIBRIN SEALANT

CROSS-REFERENCE TO RELATED APPLICATIONS

This application is a divisional of Ser. No. 16/412,487 filed on May 15, 2019, which is a divisional of U.S. application Ser. No. 14/668,341 filed on Mar. 25, 2015, now U.S. Pat. No. 10,433,825, which claims the benefit of U.S. provisional application 61/970,929 and IL application 231792 both filed on Mar. 27, 2014, the complete disclosures of which are hereby incorporated herein by reference for all purposes.

SEQUENCE LISTING

The instant application contains a Sequence Listing, which is submitted concomitantly with this application via EFS-Web in ASCII format and is hereby incorporated by reference in its entirety. Said ASCII copy, created on Dec. 22, 2013, is named "sequencelisting" and is 8 kilobytes in size.

FIELD OF THE INVENTION

The present disclosure relates to devices, systems, methods and kits for preparing and delivering a fibrin sealant.

BACKGROUND

Fibrin sealants, also known as fibrin glues, have been in use for decades (see, for example, Tabélé, et al. Organic Glues or Fibrin Glues from Pooled Plasma: Efficacy, Safety and Potential as Scaffold Delivery Systems. J Pharm Pharmaceut Sci 2012, 15:124-140; Dickneite, G et al. A comparison of fibrin sealants in relation to their in vitro and in vivo properties. Thrombosis Res 2003, 112:73-82).

Oftentimes, fibrin sealants consist of two components, a fibrinogen comprising component and a thrombin comprising component, that are delivered to a target area separately by using a double-barreled delivery device, e.g., as described in U.S. Pat. Nos. 4,874,368, 4,978,336, 5,104,375, 6,234,994 and EP-B-0 037 393, PCT Patent Application WO2007059801, U.S. Pat. Nos. 6,613,020, and 6,783,514.

Typically, a fibrin sealant clot is formed by enzymatic reactions involving fibrinogen, thrombin and Factor XIII. The thrombin converts the fibrinogen to fibrin by an enzymatic action at a rate determined by the concentration of thrombin. Factor XIII, an enzyme of the blood coagulation system, cross-links and stabilizes the fibrin clot. This process bypasses most of the steps of normal coagulation and mimics its last phase.

Some manufacturers add anti-proteolytic agents to the fibrin glue formulation (e.g. as described in PCT Patent Application WO93/05822) or specifically remove the plasminogen in order to stop or delay fibrinolysis (e.g. as described in U.S. Pat. Nos. 5,792,835 and 7,125,569). The thrombin component comprises the enzyme thrombin, which can be from human or animal (e.g. bovine or porcine) origin or produced by recombinant technology. The fibrinogen component comprises the thrombin substrate, fibrinogen, which can be from human or animal (e.g. bovine or porcine) origin or produced by recombinant technology.

Upon mixing the two components, thrombin cleaves fibrinogen thus allowing the latter to polymerize into fibrin and produce the sealant.

In prior art devices, two supply reservoirs, each containing one adhesive/sealant component, are held together by a holding device which makes it possible to hold the application device between the fingers of a hand and to operate the device by one hand.

A prior art device referred to herein as a "multi-component" device may include multiple syringes e.g. two syringes. For example, the fibrinogen component within a first syringe comprises Factor XIII and fibrinogen, and the thrombin component within a second syringe e.g. as described in U.S. Pat. No. 4,978,336. Typically, the plungers of the first and second syringes are simultaneously engaged e.g. by a coupling element and motion of the coupling element in a dispensing direction causes each engaged plunger to longitudinally slide within its respective syringe barrel so that the plungers are depressed at the same time and speed. Mixture of the two components results in a spontaneous formation of a fibrin clot, which may be used as a surgical glue.

When referring to a "multi-component" device, the term "component" refers to a protein mixture contained within a reservoir e.g. a syringe. Thus, "multi-component" device require multiple reservoirs where a different protein mixture is respectively present within each reservoir.

Oftentimes, prior art devices also include an application tip installed on the dispensing end of the device where respective outflows from the syringes are mixed. After leaving the syringes, the outflows are maintained separate from each other, and are only mixed at the exit of the tip. Nevertheless, because the two components immediately form a clot when mixed together, maintaining a steady outflow of liquid from the device is critical, to prevent the tip from getting blocked.

SUMMARY OF THE INVENTION

Embodiments of the present invention relate to a "single-component" syringe-based device for preparing and delivering/administering a fibrin sealant by passing, through a resin bed e.g. Size Exclusion desalting chromatographic media, a liquid mixture comprising: (i) fibrin (e.g. in monomeric, dimeric and/or oligomeric form) or (ii) fibrinogen and Factor II. Passage of the liquid mixture through the resin bed (i) increases the concentration of small-molecule inducer(s) of fibrin clot formation within the mixture and/or (ii) reduces the concentration of small-molecule inhibitor(s) of fibrin clot formation within the mixture.

The term "increase" refers to a concentration raise of small-molecule activator(s) within the mixture to a concentration that initiates, facilitates and/or accelerates fibrin clot formation with a clotting time ($T_{CLOT}$) of at most 1 hour at an ambient temperature between 21° C. and 25° C. In one embodiment, fibrin clot is formed at a temperature of approximately 37° C.

The term "reduce" refers to a decrease in the concentration of small-molecule inhibitor(s) within the mixture to a concentration that allows a fibrin clot formation with a clotting time ($T_{CLOT}$) of at most 1 hour at an ambient temperature between 21° C. and 25° C. In one embodiment, fibrin clot is formed at a temperature of approximately 37° C.

Typically, when a mixture is passed through and/or contacted with a pre-equilibrated resin bed (e.g. equilibrated prior to packaging of the device), an efficient buffer exchange will result in an eluent mixture (e.g. the mixture obtained following passage through the resin bed) comprising a concentration of at least 90% of the pre-equilibration buffer and/or in a reduction in the concentration of small molecules inhibitors within the mixture to lower than 10% as compared to their initial concentration within the mixture. Those skilled in the art will appreciate that by modifying the concentrations of small molecule(s) inhibitor(s) and/or activator(s), also lower buffer exchange efficiency may result in clot formation.

In one embodiment, the device is equilibrated by the user with an appropriate buffer (e.g. the buffer to be included in the resin bed depending on the mixture formulation to be applied) prior to use.

Accordingly, in one embodiment, following passage of the mixture through the resin bed, the concentration of the inhibitor(s) is decreased to lower than 50% (e.g. lower than 10%) as compared to their initial concentration within the mixture. In one embodiment, following passage of the mixture through the resin bed, the concentration of the activator(s) in the mixture is increased to at least 50% (e.g. at least 90%) of the concentration of the activator(s) in the pre-equilibration buffer. A liquid mixture comprising fibrin may include fibrin monomers, dimers and/or oligomers having a number of fibrin units so that the fibrin is maintained in soluble form in an aqueous liquid solution at an ambient temperature selected from the group consisting of about 21, 22, 23, 24, and 25° C. In one embodiment, an oligomer contains up to 10 fibrin units.

In one embodiment, following passage of the liquid mixture through the resin bed, a fibrin sealant is delivered and/or applied to the surface and a fibrin clot/polymer is formed.

For most intents and purposes, the terms "fibrin sealant", "fibrin glue", "fibrin adhesive", "fibrin clot", and "fibrin polymer" may be used interchangeably. The term "fibrin polymer" as used herein includes a plurality of fibrin units having a number of fibrin units that limit the solubility of the fibrin in an aqueous liquid solution at an ambient temperature selected from the group consisting of about 21, 22, 23, 24, and 25° C.

In contrast to the conventional "multi-component" devices discussed above, there is no need to maintain a first protein mixture within a first reservoir and a second protein mixture within a second reservoir. Instead, it is possible to employ a "single-component" scheme where only a single protein-containing reservoir is necessary. As discussed below, upon passage of the protein-containing mixture from this reservoir/container through the resin bed a fibrin clot is formed with a clotting time ($T_{CLOT}$) of at most 1 hour at an ambient temperature between 21° C. and 25° C.

"Ambient temperature" is the temperature in the area surroundings the mixture. In some embodiments, in contrast to the rapidly-clotting fibrin sealant formed in prior art devices, the clotting time ($T_{CLOT}$) of fibrin sealant formed by passing the liquid mixture through the resin bed may be at least 30 seconds or at least 1 minute, allowing for the provision of a "clog-less" and "block-less" device—i.e. during normal operation of the device, the risk of the device getting clogged up or blocked by clot formation is low as compared to the prior art devices discussed above. Instead of forming a fibrin clot by mixing multiple protein mixtures with each other, it is possible to achieve fibrin clot from a single protein mixture by passing this mixture through the resin bed so as to (i) reduce the concentration of inhibitor(s) of fibrin clot formation that is present within the mixture and/or (ii) increase the concentration of inducer(s) of fibrin clot formation within the mixture. In this sense, the presently disclosed device may be termed a "single-component" device since only a single protein mixture is required, even if different types of proteins may be present within this single mixture. The term "single-component" is interchangeable with the term "one-component".

Thus, in some embodiments, passage of the mixture through the resin bed subjects the mixture to a buffer exchange process whereby the bulk majority of inhibitory small molecules of the mixture are removed, while retaining the active proteins e.g. I) fibrin or II) fibrinogen and factor II. In some embodiments, passage of the mixture through the resin bed may supplement the mixture with inducer(s)/activator(s) small molecules such as calcium ions that may either induce and/or accelerate fibrin clot formation. The term "inducer" herein is interchangeable with the terms "initiator" and "activator".

As noted below, in a syringe implementation, the amount of force required to drive the protein mixture through the resin bed is relatively small, and can be applied by a human thumb power. As such, the presently disclosed devices may, in some embodiments, form a viable alternative to the multi-component devices of the prior art discussed above. In one non-limiting example (for example, related to syringe-based implementations), the presently disclosed device may be operated using a single hand, for example, during surgery, to produce a surgical glue.

In some embodiments relating to syringe-based implementations, (i) the liquid mixture (i.e. comprising: I-fibrin or II-fibrinogen and Factor II) is disposed/contained within a barrel of the syringe, and (ii) the syringe barrel is attached or attachable to a vessel within which the resin bed is stored. When the interior of the syringe barrel is in fluid communication with the resin bed, depression of the syringe plunger expels the liquid mixture from the syringe barrel and forces the liquid mixture to pass through the resin bed. Passage of the mixture through the resin bed results in fibrin clot formation with a clotting time ($T_{CLOT}$) of at most 1 hour at an ambient temperature selected from the group consisting of 21° C., 22° C., 23° C., 24° C., and 25° C.

In one embodiment, following passage through the resin bed, a fibrin clot is formed having a clotting time of at most 1 hour at an ambient temperature of approximately 37° C.

In one embodiment, a liquid mixture comprising fibrin monomers, dimers and/or oligomers is sustained in neutral pH and comprises a reversible fibrin polymerization blocking agent e.g. a GPRP (SEQ ID NO: 1) peptide as elaborated below.

In another embodiment, a liquid mixture comprising fibrin monomers, dimers and/or oligomers is sustained in an acidic pH as elaborated below.

A "neutral" pH is, for example, a pH of about 6-8, or pH about 6.5-7.5 or pH about 6.7-7.2. An "acidic" pH is, for example, a pH of lower than 4.

In contrast to conventional "multi-component" devices, in some embodiments, all of the proteins used for producing the fibrin sealant may be supplied from the interior of a single syringe barrel, obviating the need to maintain multiple segregated protein mixtures, and then mix them with each other in order to produce and deliver the fibrin sealant.

In some preferred embodiments of the present invention, before passing through the resin bed, the liquid mixture comprising (i) fibrin or (ii) fibrinogen and Factor II and residing within the barrel of the syringe, is "stable"—i.e. not capable of forming a fibrin polymer ("fibrin clot") on its own for a period of at least 2 weeks. Passage through the resin bed will result in clot formation.

As noted above, in some embodiments, only a "minimal" force is required to pass the mixture through the resin bed. This may be true because only a relatively short resin bed is required to initiate clot formation. Not wishing to be bound by theory, in some embodiments, passage through the resin bed may separate the relatively large proteins (e.g. proteins larger than 20 kDa) from small molecule inhibitors of fibrin clot formation and/or add small molecule inducers of fibrin clot formation. Because of the substantial molecular weight disparity between the proteins and inhibitors, e.g., arginine and citrate, only a relatively short resin bed is required for this process.

In one embodiment, the inhibitor(s) are reversible inhibitors e.g. low affinity inhibitors having no permanent effect. Therefore, typically dilution and/or small molecule exchange will remove the inhibitory effect.

In one aspect, the invention relates to a device for preparing and delivering fibrin sealant to a surface, the device comprising: a. a syringe comprising a barrel and a plunger, wherein the barrel contains a quantity of a liquid mixture (e.g. cell-free) comprising: I. fibrin or II. fibrinogen and Factor II; and b. a resin bed disposed within a vessel such that when an interior of the syringe barrel is in fluid communication with the resin bed, expulsion of the mixture from the barrel by the plunger forces the mixture to pass through the resin bed within the vessel resulting in (i) reduction in a concentration of an inhibitor(s) of fibrin clot formation within the mixture and/or (ii) increase in a concentration of an inducer(s) of fibrin clot formation within the mixture, wherein (A) following the passage through the vessel, a fibrin clot is formed with a clotting time ($T_{CLOT}$) of at most 1 hour (or at most 50 minutes, or at most 40 minutes, or at most 30 minutes, or at most 20 minutes and/or at least 5 seconds, or at least 10 seconds, or at least 30 seconds, or at least 1 minute, or at least 3 minutes, or at least 5 minutes, or at least 10 minutes, or at least 15 minutes) at an ambient temperature selected from the group consisting of 21° C., 22° C., 23° C., 24° C., and 25° C.; and (B) the inhibitor(s) and the inducer(s) are small molecules.

In another aspect, the invention relates to a system for preparing and delivering fibrin sealant to a surface, the system comprising: a. a quantity of liquid mixture (e.g. cell-free) disposed within a container e.g. a barrel of a syringe, the liquid mixture comprising: I. fibrin or II. fibrinogen and Factor II; and b. a resin bed disposed within a vessel, the vessel capable of being in fluid communication with the container, wherein when in fluid communication, passage of the mixture through the vessel (i) reduces a concentration of an inhibitor(s) of fibrin clot formation within the mixture and/or (ii) increases a concentration of an inducer(s) of fibrin clot formation within the mixture, so that after the passage of the mixture through the vessel, a fibrin clot is formed with a clotting time ($T_{CLOT}$) of at most 1 hour (or at most 50 minutes, or at most 40 minutes, or at most 30 minutes, or at most 20 minutes and/or at least 5 seconds, or at least 10 seconds, or at least 30 seconds, or at least 1 minute, or at least 3 minutes, or at least 5 minutes, or at least 10 minutes, or at least 15 minutes) at an ambient temperature selected from the group consisting of 21° C., 22° C., 23° C., 24° C., and 25° C., wherein the inhibitor(s) and the inducer(s) are small molecules.

In another aspect, the invention relates to a kit comprising: a. a quantity of a liquid mixture (e.g. cell-free) disposed within a container, the liquid mixture comprising: I. fibrin or II. fibrinogen and Factor II; and b. a resin bed disposed within a vessel, the vessel capable of being in fluid communication with the container, such that when the container and the vessel are in fluid communication, the passage of the mixture through the vessel (i) reduces a concentration of an inhibitor(s) of fibrin clot formation within the mixture and/or (ii) increases a concentration of an inducer(s) of fibrin clot formation within the mixture, so that after the passage of the mixture through the vessel, a fibrin clot is formed with a clotting time ($T_{CLOT}$) of at most 1 hour (or at most 50 minutes, or at most 40 minutes, or at most 30 minutes, or at most 20 minutes and/or at least 5 seconds, or at least 10 seconds, or at least 30 seconds, or at least 1 minute, or at least 3 minutes, or at least 5 minutes, or at least 10 minutes, or at least 15 minutes) at an ambient temperature selected from the group consisting of 21° C., 22° C., 23° C., 24° C., and 25° C., wherein the inhibitor(s) and the inducer(s) are small molecules.

In another aspect, the invention relates to a method for preparing and delivering a fibrin sealant to a surface, the method comprising: a. providing a quantity of a liquid mixture (e.g. cell-free) comprising: I. fibrin or II. fibrinogen and Factor II; and b. passing the mixture through a resin bed so as to (i) reduce a concentration of an inhibitor(s) of fibrin clot formation within the mixture and/or (ii) increase a concentration of an inducer(s) of fibrin clot formation within the mixture, so that after the passage of the mixture through the resin, a fibrin clot is formed with a clotting time ($T_{CLOT}$) of at most 1 hour at an ambient temperature selected from the group consisting of 21° C., 22° C., 23° C., 24° C., and 25° C., wherein the inhibitor(s) and the inducer(s) are small molecules.

In one embodiment, a fibrin clot is formed with a clotting time ($T_{CLOT}$) of at most 1 hour at an ambient temperature in the range of about 20° C. to 40° C. e.g. 21° C. to 37° C.

In another aspect, the invention relates to a device configured to generate a fibrin sealant from a liquid mixture comprising fibrinogen and Factor II, the mixture stored within a reservoir of the device, wherein
  (i) the device operates as a clog-less and block-less device; and
  (ii) a fibrin clot is formed with a clotting time ($T_{CLOT}$) of up to about 1 hour (e.g. about 10 seconds to about 1 hour or 10 minutes to about 1 hour) at an ambient temperature selected from the group consisting of 21° C., 22° C., 23° C., 24° C., and 25° C.

In one embodiment, in the case that the fibrin sealant is applied to a surface comprising Tissue Factor and/or phospholipids e.g. injured tissue, a fibrin clot is formed with a clotting time of about 10 seconds to about 10 minutes.

In another aspect, the invention relates to a device configured to generate a fibrin sealant from a liquid mixture comprising fibrin and a reversible fibrin polymerization blocking agent, the mixture stored within a reservoir of the device, wherein
  (i) the fibrin in the liquid mixture is in the form of monomers and/or oligomers;
  (ii) the device operates as a clog-less and block-less device; and
  (iii) a fibrin clot is formed with a clotting time ($T_{CLOT}$) in the range of about 5 seconds to about 1 hour at an ambient temperature selected from the group consisting of 21° C., 22° C., 23° C., 24° C., and 25° C.

Also, disclosed herein is a clog-less and block-less device configured to generate fibrin sealant from a liquid mixture comprising fibrinogen and Factor II, the mixture is stored within a reservoir/container e.g. syringe barrel of the device, wherein following the passage through the resin bed, a fibrin clot is formed with a clotting time ($T_{CLOT}$) of up to about 1 hour (e.g. in the range of about 10 seconds to about 1 hour or in the range of about 10 minutes to about 1 hour) at an ambient temperature selected from the group consisting of 21° C., 22° C., 23° C., 24° C., and 25° C. In some embodiments, the liquid mixture further comprises Factor X, Factor VII, Factor IX and optionally their associated cofactors (e.g. Factor V, Factor VIII).

Also, disclosed herein is a clog-less and block-less device configured to generate fibrin sealant from a liquid mixture comprising fibrin (in monomeric, dimeric and/or oligomeric form) and a reversible fibrin polymerization blocking agent e.g. GPRP (SEQ ID NO:1) the mixture is stored within a reservoir of the device, wherein following the passage through the resin bed, a fibrin clot is formed with a clotting time ($T_{CLOT}$) in the range of about 5 seconds to about 1 hour at an ambient temperature selected from the group consisting of 21° C., 22° C., 23° C., 24° C., and 25° C.

In some embodiments, the device, system and/or kit according to the invention is used to deliver fibrin sealant to a surface.

In some embodiments (e.g. relating to any device, system, kit and/or method disclosed herein), before passing the mixture through the resin bed, the liquid mixture within the syringe barrel is stable for at least two weeks.

In some embodiments (e.g. relating to any device, system, kit and/or method disclosed herein), the resin bed is a packed bed.

In some embodiments (e.g. relating to any device, system, kit and/or method disclosed herein), the device further comprises a tip capable of being in fluid communication with a distal end of the vessel so that, when in fluid communication, the fibrin sealant is delivered through the tip to the surface. The liquid mixture can be applied, for example, by dripping, spraying (e.g. by including a shared nozzle with a pressurized gas container) and/or spreading.

In some embodiments (e.g. relating to any device, system, kit and/or method disclosed herein), the container (e.g. a syringe barrel) and the vessel are mechanically coupled to each other so that respective interiors thereof separated by a removable barrier and/or at least one of (i) a septum, (ii) one way filter, (iii) a valve, and (iv) stopcock.

In some embodiments (e.g. relating to any device, system, kit and/or method disclosed herein), the container and the vessel are detachably attachable. In another embodiment, the container and the vessel are integrally formed as a monolithic piece. In some embodiments (e.g. relating to any device, system, kit and/or method disclosed herein), the container and the vessel are parts of a monolithic piece—e.g. a flexible monolithic piece.

In some embodiments (e.g. relating to any device, system, kit and/or method disclosed herein), a majority of the force required to pass the liquid mixture through the resin bed is provided by a human thumb muscle power.

In some embodiments (e.g. relating to any device, system, kit and/or method disclosed herein), (i) the clotting time ($T_{CLOT}$) is at most 50 minutes, or at most 40 minutes, or at most 30 minutes, or at most 20 minutes and/or (ii) at least 5 seconds, or at least 10 seconds, or at least 30 seconds, or at least 1 minute, or at least 5 minutes, or at least 10 minutes, or at least 15 minutes.

In some embodiments (e.g. relating to any device, system, kit and/or method disclosed herein), a ratio between: i. a concentration of 20+ kDa proteins in the mixture before passage through the resin bed and ii. a concentration of 20+ kDa proteins in the fibrin sealant after passage through the resin bed, is about 1.

In some embodiments (e.g. relating to any device, system, kit and/or method disclosed herein), a ratio between: i. a concentration of 30+ kDa proteins in the mixture before passage through the resin bed and ii. a concentration of 30+ kDa proteins in the fibrin sealant after passage through the resin bed, is about 1.

In some embodiments (e.g. relating to any device, system, kit and/or method disclosed herein), the fibrin sealant is prepared from the liquid mixture after a retention time of at most 1 minute, or at most 45 seconds, or at most 30 seconds, or at most 15 seconds, or at most 10 seconds, or at most 5 seconds, or at most 3 seconds, or at most 1 second. The term "retention time" typically refers to the time it takes the liquid mixture to pass through the vessel containing the resin under set conditions.

Without being bound by the mechanism, this relatively short retention time may be due to the resin bed properties—e.g. due to factors, including but not limited to, resin volume, physical dimensions of the resin bed e.g. length and/or width/diameter, compression of packed resin bed etc.

In some embodiments (e.g. relating to any device, system, kit and/or method disclosed herein), expulsion of the liquid mixture from the container (e.g. from a syringe barrel) forces the mixture to flow through the resin bed in a manner that is substantially uniform over a cross-section of the resin bed.

In some embodiments (e.g. relating to any device, system, kit and/or method disclosed herein), the device comprises at least one mesh, the mesh configured to distribute the flow over the resin bed (e.g. in a manner that is substantially uniform over a cross-section of the resin bed) and/or retain the resin beads within the bed.

In some embodiments (e.g. relating to any device, system, kit and/or method disclosed herein), the device comprises two meshes.

In some embodiments (e.g. relating to any device, system, kit and/or method disclosed herein), the resin bed resides within the vessel such that the mixture passes through a grid and subsequently through a filter-paper en route to the resin bed, the grid configured to provide mechanical support during the application of pressure as well as spread the flow over the filter paper, and the filter-paper configured to distribute the flow over the resin bed and retain the resin beads within the bed.

In some embodiments (e.g. relating to any device, system, kit and/or method disclosed herein), a height of the resin bed is at most 10 cm, or at most 7.5 cm, or at most 5 cm or at most 2.5 cm, or at most 2 cm, or at most 1.5 cm or at most 1 cm.

In some embodiments (e.g. relating to any device, system, kit and/or method disclosed herein), a height of the resin bed is at least 0.5 cm.

In some embodiments (e.g. relating to any device, system, kit and/or method disclosed herein), a height of the resin bed is at most 10 cm, or at most 7.5 cm, or at most 5 cm, or at most 2.5 cm, or at most 2 cm, or at most 1.5 cm, or at most 1 cm. and/or at least 0.5 cm.

Not wishing to be bound by theory, in some embodiments (e.g. relating to any device, system, kit and/or method disclosed herein), because the bed is relatively short, a relatively "wide bed" may be required to achieve a sufficient buffer exchange to initiate and/or accelerate fibrin clot formation.

In some embodiments (e.g. relating to any device, system, kit and/or method disclosed herein), a width of the resin bed is at most 5 cm, or at most 2.5 cm, or at most 1.3 cm.

Oftentimes, the word "width" is interchangeable with the word "diameter".

In some embodiments (e.g. relating to any device, system, kit and/or method disclosed herein), a ratio between a height of the resin bed and a characteristic width thereof is at most 2.5, or at most 2, or at most 1.5, or at most 1 or at most 0.75 and/or at least 0.5.

In some embodiments (e.g. relating to any device, system, kit and/or method disclosed herein), the quantity of the liquid mixture within the container (e.g. syringe barrel) has a volume of at least 0.5 ml, or at least 1 ml and/or at most 15 ml, or at most 10 ml, or at most 5 ml.

In some embodiments (e.g. relating to any device, system, kit and/or method disclosed herein), the resin bed is relatively "short" so that even an average user can force the liquid mixture through the bed without any requirement of a centrifuge.

In some embodiments (e.g. relating to any device, system, kit and/or method disclosed herein), a force of at most 100 Newtons or at most 75 Newtons, or at most 50 Newtons, or at most 30 Newtons applied to the plunger over a period of time of at most 60 seconds is sufficient to force a majority of the liquid mixture stored within the container (e.g. syringe barrel) through the resin bed at a retention time of at most 60 seconds.

In some embodiments (e.g. relating to any device, system, kit and/or method disclosed herein), the resin bed is pre-packed.

In some embodiments (e.g. relating to any device, system, kit and/or method disclosed herein), the resin bed is pre-equilibrated with the inducer(s).

In one embodiment (e.g. relating to any device, system, kit and/or method disclosed herein), the resin bed is pre-equilibrated with a desired final concentration of the inhibitor(s) e.g. at a concentration lower than the initial concentration of the inhibitor(s) in the mixture. Without being bound by the mechanism, by including a fixed concentration of the inhibitor within the resin bed, one can control the concentration of the inhibitor within the mixture following passage through the device, thereby controlling fibrin polymerization rate.

In some embodiments (e.g. relating to any device, system, kit and/or method disclosed herein), the fraction of the resin bed that is in the liquid phase is at least 10%, or at least 20%, or at least 30% and/or at most 50% or at most 40% (all percentages are v/v).

In one particular example, the liquid phase of the resin bed is 30-40% of the total resin bed volume and is about equal to the volume of the liquid mixture within the container (e.g. syringe barrel).

In one embodiment (e.g. relating to any device, system, kit and/or method disclosed herein), the resin bed has a volume in the range of 0.7 ml to 20 ml.

In one embodiment, the resin bed has a volume of 6.4 ml. In another embodiment, the resin bed has a volume of 12.3 ml.

In some embodiments (e.g. relating to any device, system, kit and/or method disclosed herein), a volume ratio between (i) a volume of the liquid mixture within the syringe barrel and (ii) a volume of the resin bed is at least 0.1, or at least 0.2 and/or at most 10, or at most 5.

In one embodiment, a volume ratio between (i) a volume of the liquid mixture within the syringe barrel and (ii) a volume of the resin bed is in the range of about 0.1 to about 10. In another embodiment, a volume ratio between (i) a volume of the liquid mixture within the syringe barrel and (ii) a volume of the resin bed is in the range of about 0.2 to about 5. In another further embodiment, a volume ratio between (i) a volume of the liquid mixture within the syringe barrel and (ii) a volume of the resin bed is in the range of about 0.3 to about 1.

In some embodiments (e.g. relating to any device, system, kit and/or method disclosed herein), the resin bed is sterilizable—i.e. after sterilization the resin bed is still capable to perform its function. In some embodiments, the device and components thereof (including the liquid mixture) are sterile.

In some embodiments (e.g. relating to any device, system, kit and/or method disclosed herein), the liquid mixture comprises fibrinogen and Factor II.

In some embodiments (e.g. relating to any device, system, kit and/or method disclosed herein), the inhibitor(s) is a serine protease active site inhibitor.

In some embodiments (e.g. relating to any device, system, kit and/or method disclosed herein), the inhibitor(s) is a calcium chelator.

In some embodiments (e.g. relating to any device, system, kit and/or method disclosed herein), the inducer(s) is a cation, for example a calcium cation or other divalent cations such as magnesium, iron or zinc or combinations thereof.

In some embodiments (e.g. relating to any device, system, kit and/or method disclosed herein), the inducer(s) is a phospholipid, cephalin and/or a divalent cation.

In some embodiments (e.g. relating to any device, system, kit and/or method disclosed herein), the resin bed is pre-equilibrated with a vitamin K-dependent clotting zymogen-activating buffer solution—e.g. kaolin powder, phospholipids, cephalin, tissue factor, thromboplastin, buffers of the appropriate pH.

In some embodiments (e.g. relating to any device, system, kit and/or method disclosed herein), the resin bed comprises $CaCl_2$.

In some embodiments (e.g. relating to any device, system, kit and/or method disclosed herein), the liquid mixture comprises fibrin in monomeric, dimeric and/or oligomeric form.

In some embodiments (e.g. relating to any device, system, kit and/or method disclosed (SEQ ID NO: 1) B herein), the liquid mixture is sustained in a neutral pH, and the inhibitor is a GPRP peptide or other reversible fibrin polymerization blocking agent.

In some embodiments (e.g. relating to any device, system, kit and/or method disclosed herein), the liquid mixture is sustained in an acidic pH, and the inhibitor is a hydronium ion ($H_3O$).

In some embodiments (e.g. relating to any device, system, kit and/or method disclosed herein), the inducer(s) is hydroxyl ion (OH).

In some embodiments (e.g. relating to any device, system, kit and/or method disclosed herein), the resin bed comprises arginine.

All embodiments relate to any device, system, kit and/or method disclosed herein.

DETAILED DESCRIPTION OF THE INVENTION

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

Figure 1A:
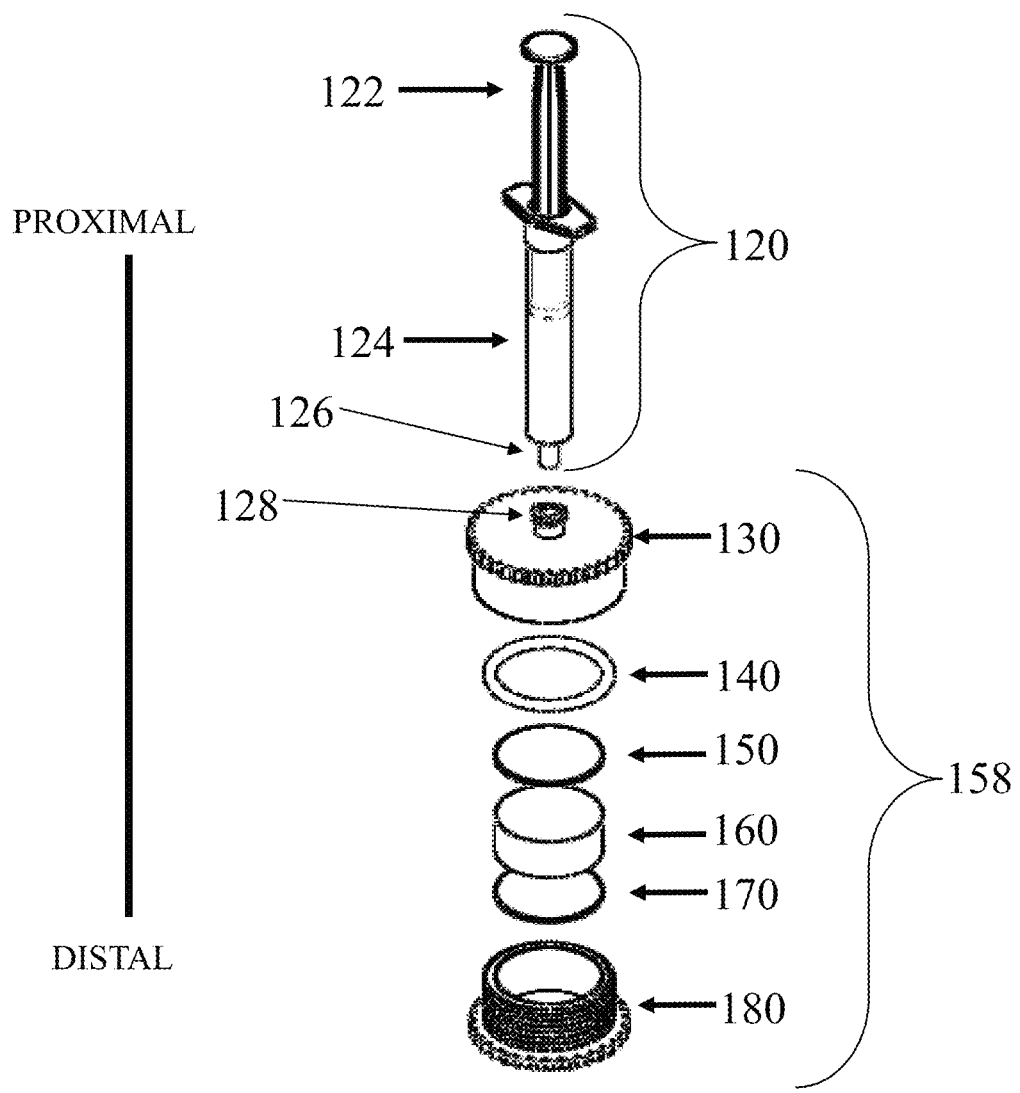
FIGS. 1A and 1B are exploded and front views of an exemplary device for preparing and delivering a fibrin sealant according to some embodiments.
Figure 1B:
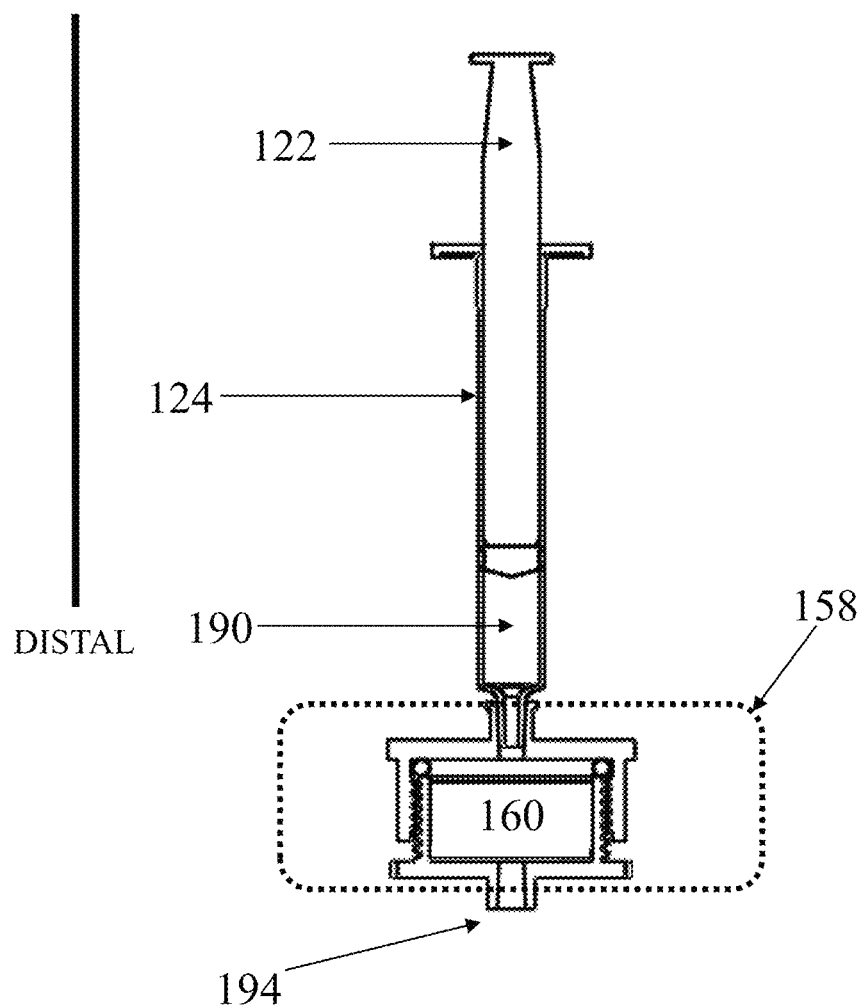

FIGS. 1A and 1B are exploded and front views of a device for preparing and delivering a fibrin sealant. According to the non-limiting example of FIGS. 1A-1B, the device includes: (i) a syringe 120; (ii) a vessel 158; and (iii) resin bed 160 disposed within the vessel 158. Syringe 120 comprises (i) a plunger 122 and (ii) a barrel 124 including a tip 126 for the attachment of the syringe to the vessel (e.g. a male Leuer-Lock fitting). Tip 126 is dimensioned to mate with socket 128 (e.g. to form a liquid-tight seal), and is not to be confused with the application tip (not shown) located distal to resin bed 160.

In the specific example of FIG. 1, vessel 158 comprises proximal 130 and distal 180 housing portions. Disposed within vessel 158 are (i) O-ring 140; (ii) proximal 150 and distal 170 filter paper; and (iii) resin bed 160. As illustrated in FIG. 1B, vessel 158 has a male Leuer-Lock adaptor which is the distal port 194.

Also illustrated in FIG. 1B is a quantity of a liquid mixture 190 (e.g. a cell-free mixture such as a protein mixture prepared from the acellular plasma portion of blood or by recombinant techniques) comprising: (i) fibrin or (ii) fibrinogen and Factor II.

This liquid mixture is disposed within the barrel 124 of syringe 120. In some embodiments, when mixture 190 is within syringe barrel 124, mixture 190 is considered "stable"—e.g. not capable of forming fibrin polymer ("fibrin clots") on its own for a time period of at least 2 weeks.

Passage of the mixture 190 (e.g. after it is expelled from the barrel 124 of syringe 120) through resin bed 160 results in: (i) reduction in a concentration of an inhibitor(s) of fibrin clot formation that is present within the mixture and/or (ii) increase in a concentration of an inducer(s) of fibrin clot formation within the mixture, wherein the inhibitor(s) and the inducer(s) are small molecules. In some embodiments, depression of plunger 122 expels mixture 190 from syringe barrel 124 (e.g. via tip 126) and forces the expelled mixture 190 through resin bed 160.

Figure 2A:
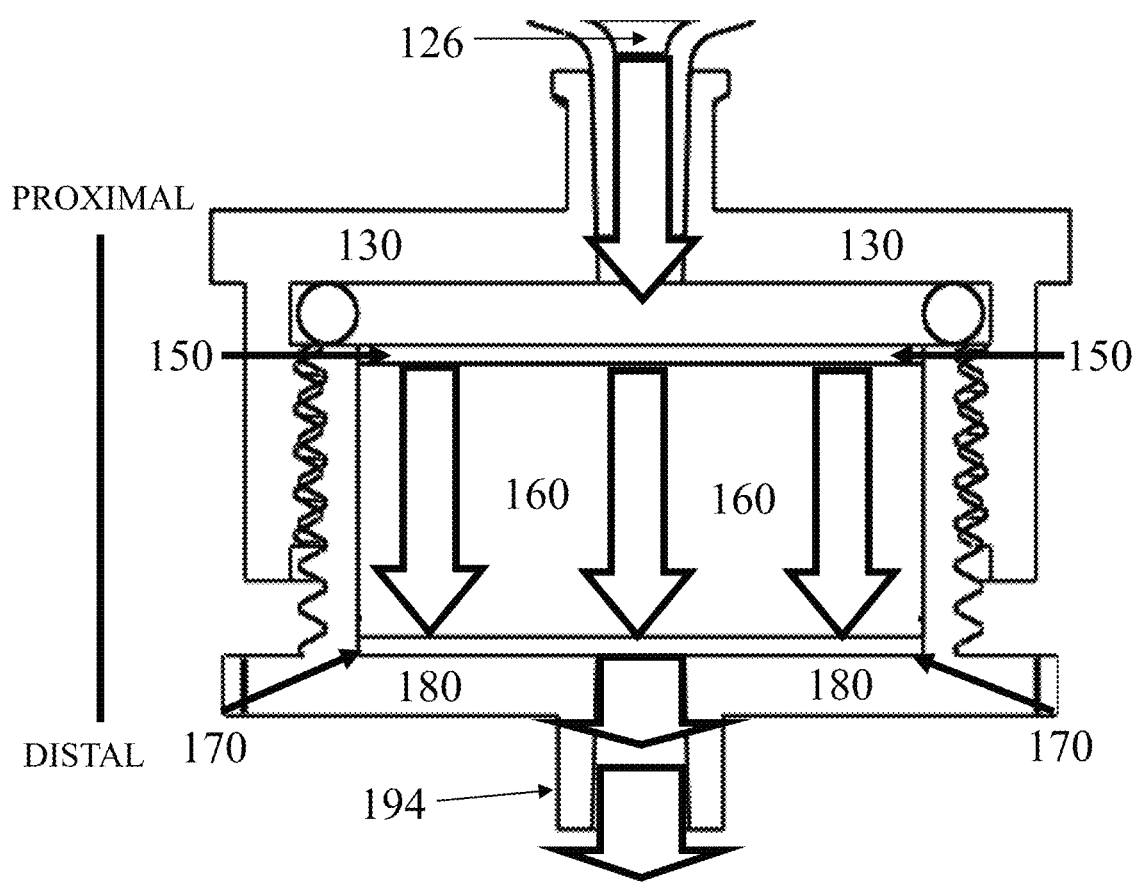
FIG. 2A illustrates passage of a liquid mixture through a resin bed within a vessel.
Figure 2B:
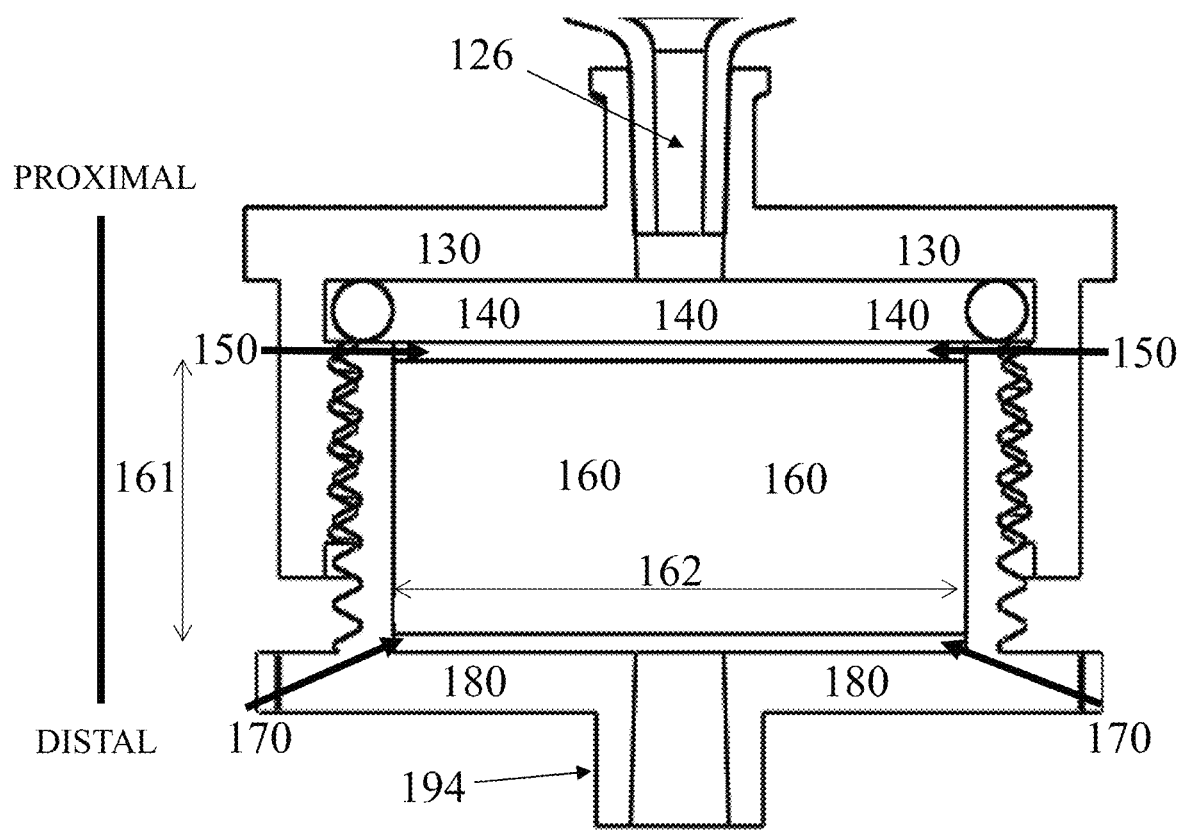
FIG. 2B illustrates an O-ring, proximal filter paper, a resin bed, and distal filter paper disposed within a vessel.

FIGS. 2A-2B are close-up illustration of the assembled vessel 158 within which resin bed 160 is disposed. FIG. 2A illustrates passage of the mixture 190 through resin bed 160 within vessel 158. FIG. 2B illustrates an O-ring 140, proximal filter paper 150, a resin bed 160, and distal filter paper 170 disposed within a vessel 158. The O-ring 140 may prevent leakage e.g. from the juxtaposition between the spiral etchings of the proximal 130 and distal 180 housing portions that comprise the screwable element. In the embodiment of FIGS. 2A-2B, a vessel is assembled from proximal and distal housing portions that are screwably attachable to each other. In another embodiment, the proximal and distal portions of the housing are mechanically attachable.

The housing can be composed of a plastic material e.g. polypropylene, polycarbonate, Acrylonitrile-Butadiene-Styrene (ABS), the like and a combination thereof. The O-ring can be composed of an elastomer such as silicone; rubber and fluoropolymer elastomer; rubber; and/or Nitrile Butadiene Rubber (NBR) and the like.

In one embodiment, the device comprises filters 150 and 170 e.g. Watmann GF flanked at each side with a support grids (e.g. Support Screen for Columns i.d. 26 mm; Product code: 18-9377-01; GE Healthcare, Sweden). In such an embodiment, one support grid is located proximal to filter paper 150 and the other is located distal to filter paper 170. The support grid may provide a mechanical support for the filters.

The support grid can be composed of polypropylene, polyethylene, polyamide, Teflon, and/or stainless steel and the like.

FIG. 2A illustrates passage of the mixture 190 through resin bed 160 within vessel 158. The results according to the invention show that the device according to the invention comprises a resin bed having a height to width ratio (e.g. 0.52 or 1) so that advantageously it can be manipulated by the force applied by a human thumb muscle power and yet provide an efficient buffer exchange as known commercial gel filtration spin columns (e.g. Disposable PD-10 Desalting Columns, Product code: 17-0851-01, GE Healthcare, Sweden). Typically, commercial gel filtration spin column are long and narrow (e.g. having a height:width ratio of about >3). In order to pass a mixture through such commercial columns, either a long processing time (when utilizing gravity) or significant force (e.g. using a centrifuge) is required. These commercially available columns are typically not compatible with hand-held devices (e.g. a syringe). Accordingly, in some embodiments, it may be desirable to employ a resin bed of minimal height, for example, in order to minimize the amount of force required to pass the mixture 190 through resin bed 160. As such, it may be preferred to use a resin bed where a ratio between (i) a height (161 in FIG. 2B) of the resin bed and (ii) a characteristic width (162 in FIG. 2B) thereof is at most about 2.5 or at most about 2 or at most about 1.5 or at most about 1 or at most about 0.75 and/or at least 0.5. In one embodiment, the resin bed has a diameter (width) of 25 mm and a height of 13 mm i.e. —a height to width ratio of 0.52. In another embodiment, the resin bed has a diameter (width) of 25 mm and a height of 25 mm i.e. —a height to width ratio of 1.

As such, in order for mixture 190 to "interact" or "contact" with substantially the entire resin bed, it may desirable to achieve a relatively uniform flow over a cross-section of resin bed 160 so that the mixture flows through the entire resin bed. This flow profile is illustrated in FIG. 2A.

The term "contact" or "interact" refer to any type of a combining action which brings the mixture into sufficiently close contact with the resin bed in a manner that the solutes/small molecules are removed and/or exchanged as they are passed through the resin bed. The mixture can be incubated within the resin bed for a sufficient period of time which allows solutes/small molecules removal and/or exchange. The mixture can be in a temperature in the range of 20° C. to 40° C. while passing through the resin bed and a pH in the range of 6 to 8 while exiting the device.

Filter paper 150 may function to assist in the flow distribution over resin bed 160. Another function of proximal filter paper 150, together with distal filter paper 170, may be to retain bead particles within resin bed 160.

Filter paper is one example of a mesh—in different embodiments, other mesh structures (i.e. other than filter paper) can be used to assist in flow distribution over the cross section of resin bed 160 and/or to retain bead particles within resin bed 160.

In some embodiments, the mesh size (i.e. the size of the pores therein) is at least 2-fold smaller than the size of the smallest bead. In one embodiment, the mesh size is between 10-20 micrometers. "Mesh" relates to any type of a porous matrix that may assist in flow distribution over the cross section of resin bed 160 and/or to retain bead particles within resin bed 160. Non limiting examples of meshes are grids, etched materials, polymer networks, filters and the like. Meshes can be composed of any material e.g. biocompatible material such as plastic, nylon, cellulose, alloys, glass and the like. The device can comprise more than one mesh element.

Those skilled in the art will appreciate that a typical packed resin bed may be comprised of approximately 60-70% (v/v) solid material, and the remaining 30-40% (v/v) is comprised of a liquid solution which contains the small molecule solutes or of any other ratio of solid material and liquid solution. In one embodiment, the packed resin bed is comprised of approximately 60-70% (v/v) solid material, and the remaining 30-40% (v/v) is comprised of a liquid solution which contains the small molecule solutes. The small molecules in the liquid mixture are removed and/or exchanged when a volume of the liquid mixture 190 comprising proteins is driven through the device as described. Thus, the protein solution is exuded from the device having a substantially similar volume as before passage through resin bed 160 and with minor changes in protein composition, whereas the solutes/small molecules are removed and/or exchanged as they are passed through the resin.

In some embodiments, before entering vessel 158, mixture 190 is considered to be "stable". Passage of mixture 190 through the resin bed 160 and through vessel 158 allows sealant formation having a clotting time ($T_{CLOT}$, a time parameter) of at most 1 hour at an ambient temperature selected from the group consisting of 21° C., 22° C., 23° C., 24° C., and 25° C. In some embodiments, a value of $T_{CLOT}$ is at most 1 hour, or at most 50 minutes, or at most 40 minutes, or at most 30 minutes, or at most 20 minutes.

Alternatively or additionally, a value of $T_{CLOT}$ is at least 5 seconds, or at least 10 seconds, or at least 30 seconds, or at least 1 minute, or at least 3 minutes, or at least 5 minutes, or at least 10 minutes, or at least 15 minutes.

In some embodiments, after passage through resin bed 160, mixture 190 may be used as a surgical glue.

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

Unless specified otherwise, for the present disclosure, when two quantities $QUANT_1$ and $QUANT_2$, are "about" equal to each other or "substantially equal" to each other, the quantities are either exactly equal, or a "quantity ratio" between (i) the greater of the two quantities MAX ($QUANT_1$, $QUANT_2$) and (ii) the lesser of the two quantities MIN($QUANT_1$, $QUANT_2$) is at most 1.3. In some embodiments, this ratio is at most 1.2 or at most 1.1 or at most 1.05. In the present disclosure, "about" equal and "substantially equal" are used interchangeably and have the same meaning.

A "small-molecule" inducer/activator or inhibitor has a molecular weight of up to 1,000 daltons. Non limiting examples of "small-molecules" include ions, short peptides having less than 8 amino acids and compounds.

In some embodiments, the small-molecule inhibitor is an isolated peptide, a derivative or salt thereof, which is capable of reversibly binding a fibrin monomer and prevent or delay fibrin clot formation. In some embodiments, the small molecule inhibitor is a small chemical molecule. The small molecule inhibitor may be a low affinity binding agent to fibrin monomers having no permanent effect on fibrin polymerization. Therefore, typically dilution and/or small molecule exchange will initiate polymerization.

In some embodiments, the inhibitor is selected from the group consisting of a calcium chelator, a serine protease active site inhibitor and a combination thereof.

In some embodiments, the small molecule activator/inducer is a divalent cation e.g. a calcium cation. In some embodiments, the calcium cation is provided by $CaCl_2$.

A "resin bed" refers to a plurality of matrices fabricated in the form of beads (e.g. in submillimetric to micrometric size) from polymer substrates (e.g. sepharose, agarose, acrylate) sustained in a liquid e.g. buffer. Resins are well known in the art e.g. as described in "Protein Liquid Chromatography" edited by: Michael Kastner. Journal of Chromatography Library—volume 61 Elsevier Science, 2000; pages 94-114. The resin bed is used as a small molecule exchanger also known as "size exclusion" resin. Typically, small molecule exchange is the replacement of one set of small molecules with another set. Oftentimes, the resin is pre-equilibrated with the small molecules that initiate and/or accelerate fibrin clot formation. Resin bed typically refers to the liquid phase e.g. including solutes and the solid phase i.e. resin beads of the resin bed.

The beads can be composed of a hydrophilic material such as agarose, sepharose, acrylic beads, cellulose, controlled pore glass, silica gels, dextranes; hydrophobic material; or an organic artificial/synthetic polymer such as materials based on polyacrylamides or polystyrens. Typical materials/polymers are commercially available under the trade names Sephacryl®, Sephadex®, Superdex® (GE Healthcare, Sweden), Ultragel® (Biosepara, France) TSK-Gel Toyopearl® (Tosoh Corp., Japan), HEMA (Alltech Ass. (Deer-field, Ill., USA), Eupergit® (Rohm Pharma, Darmstadt, Germany). Also materials based on azlactones (3M, St. Paul, Minn., USA). In one embodiment, the beads are composed of Agarose® or Sepharose® or Sephadex®. These materials are commercially available. Typically, the resin is an insoluble matrix fabricated from an organic polymer substrate. Without wishing to be bound to theory, the resin beads are typically porous, the pores being in the range of molecular weights of those molecules which are to be replaced. The proteins in the mixture will be too large to enter the pores of the resin and will quickly pass through the resin bed. In contrast, small molecules in the mixture e.g. the inhibitors will travel a more tortuous route, as they are able to enter and re-exit the pores of the resin, thus greatly slowing their rate of migration through the resin bed. Those small molecules with which the resin has been pre-equilibrated e.g. inducer(s) enjoy an advantage of a significant "head-start", and therefore exit the resin together with the proteins. Thus, the buffer salts and other small molecules are exchanged in this step. This technique is known by several names depending on the specific application e.g. "gel filtration", "desalting" and "buffer exchange".

In some preferred embodiments, the bed is a "packed bed". Typically, a "packed bed" refers to a situation wherein within a resin bed, beads are substantially homogenously distributed in regards to their size. The bed is compressed (condensed under pressure) so that the beads are brought into contact without significantly deforming their structure. The skilled in the art will appreciate that optimal compression ratios are empirically determined, known and differ between the different resins. In some embodiments, the compression ratio is of (i) at least 5%, or at least 10%, or at least 20% and/or (ii) at most 40%. In one embodiment, the size of the beads is given as a distribution of sizes between 15-90 microns (super-fine resins) and up to 80-500 microns (coarse resins). Examples of appropriate beads include, but are not limited to, sepharose, agarose, acrylate.

It was shown that when the device according to the invention was used to passage a mixture for a second time, after washing with the pre-equilibration buffer, a reduction in the time to form a fibrin clot was observed. Without being bound to theory, the passage of liquid through the resin bed results in its compression affecting the time to fibrin clot formation.

In one embodiment, the resin used in the device is Sephadex G-25 Medium (Product code: 17-0033-01; GE Healthcare, Sweden) with the following characteristics: Matrix: Cross-linked dextran, Separation mechanism: According to size, Wet particle size range: 38 to 235 μm, Dry particle size: >50 μm, Exclusion limit (Mr): 5000, Chemical stability: All commonly used buffers, Working pH range: 2 to 13.

The term "resin bed" and "gel filtration matrix" may be used interchangeably. A "clotting time" is the time required for an observable clot to form. The clot may be observed visually, or be observed by mechanical means—e.g. by observing a cessation of flow upon inversion or tilting of the tube containing the mixture or by measuring viscosity. The clotting activity level or capability of the mixture to form a sealant can be determined in-vitro and/or in-vivo.

The term "clotting" does not necessarily require the presence of thrombin to achieve the "clotting". The term "clotting" includes also fibrin polymer formation. Clot formation can be also be determined by measuring migration length on a slanted surface (or drop test model), by using a clotting analyzer such as the Start4 clotting analyzer (Diagnostica Stago) or by any other method known in the art. Full clotting can be assessed by cessation of flow of the liquid mixture e.g. upon inversion. Rapid polymerization can be measured using a Stat4 clotting analyzer Stago Diagnostics or equivalent coagulometer. Some embodiments relate to liquid mixtures which (i) before passage through the resin bed are considered "stable" and (ii) after passage through the resin bed, have a clotting time of at most 1 hour at an ambient temperature between 21° C. and 25° C.

The term "stable", and "stability" when referring to a liquid mixture, mean substantially an absence of fibrin polymerization/clotting in the mixture before it passes through and/or contacts the resin bed.

For example, a liquid mixture comprising (i) fibrin monomers, dimers and/or oligomers or (ii) fibrinogen and Factor II may, before passage through the resin bed, be considered stable. The mixture (e.g. stored within a syringe barrel or another suitable container) may be stable due to a presence of small molecules inhibitor(s) and/or absence of small molecules inducer(s). Low pH conditions [e.g. a mixture having a hydronium ion ($H_3O$) concentration of higher than 0.1 mM/a pH lower than 4] may be considered as an embodiment of small molecule inhibitors preventing fibrin polymerization.

Non limiting examples of a stable liquid mixture comprising at least one of (i) fibrin monomers, dimers and/or oligomers or (ii) fibrinogen and Factor II.

A first example relates to a mixture comprising Factor II (also known as prothrombin which is a vitamin K-dependent clotting zymogen) and concentrated fibrinogen, and optionally other vitamin K-dependent clotting zymogens (e.g. Factor X, Factor VII, Factor IX) and optionally their associated co-factors (e.g. Factor V, Factor VIII). The ratio of Factor II or vitamin K-dependent clotting zymogens (U) to fibrinogen (mg clottable protein) can be about 0.01 to about 1.0, as normalized to Factor II.

In some embodiments, the mixture comprises fibrinogen in an effective amount of about 1 to 2 mg/ml, 1 to 110 mg/ml, 10 to 110 mg/ml such as about 40 mg/ml to 70 mg/ml.

In some embodiments, the mixture comprises Factor II in a final concentration of about 0.1 IU/ml to about 25 IU/ml e.g. 0.14 IU/ml.

In some embodiments, the mixture comprises fibrinogen; and vitamin K-dependent clotting zymogens comprising at least Factor II and Factor X; and at least one reversible small molecule inhibitor of at least one of the vitamin K-dependent clotting zymogens.

In some embodiments, the mixture is free of an added irreversible thrombin inhibitor e.g. hirudin and/or anti-thrombin III. An irreversible thrombin inhibitor comprises a group of molecules that covalently bind thrombin or bind thrombin with a very high affinity and/or a group of molecules that destroy a functional group on thrombin or render the thrombin inactive. For example, hirudin and anti-thrombin III are considered herein as such irreversible thrombin inhibitors. Thrombin binds to anti-thrombin III such that thrombin is not released from the complex. As used herein, a thrombin inhibitor that binds thrombin with a high affinity (sub-microM) is considered irreversible. One such example is hirudin, which binds thrombin in the picoM range.

In some embodiments, the mixture further comprises Factor V. The mixture may further comprise Factor VII and/or Factor IX. In some embodiments, Factor X, Factor VII, and/or Factor IX are, at least partially, in their active form.

In some embodiments, the reversible small molecule inhibitor is selected from the group consisting of a calcium chelator, a serine protease active site inhibitor and a combination thereof. In some embodiments, the mixture e.g. liquid formulation remains stable for at least 14 days (e.g. about a month, three months) at an ambient temperature of about 2° C. to 8° C. In some embodiments, the mixture remains stable at least 7 days at an ambient temperature of about 2° C. and up to room temperature.

In some embodiments, the mixture is stable for about 30 days at room temperature (20-25° C.). In some embodiments, the mixture is free of added thrombin.

The term "free of added" in connection with the terms "free of added thrombin" and "free of added irreversible thrombin inhibitor" means that the mixture is not supplemented with thrombin or irreversible thrombin inhibitor. However, it should be noted that the mixture may comprise low amounts of thrombin (e.g. less than 1 IU/ml mixture) and/or irreversible thrombin inhibitor (e.g. less than 5 µM) originally present in the mixture and/or thrombin spontaneously formed in the mixture.

In one embodiment, the vitamin K-dependent clotting zymogens used to prepare the mixture is provided as a concentrate, concentrated by about 2-50 fold compared to their concentration in plasma, as normalized to Factor II.

In one embodiment, the vitamin K-dependent clotting zymogen concentrate used to prepare the mixture is a PPSB concentrate [an acronym for: Factor II (prothrombin); Factor VII (proconvertin), Factor X (Stuart Factor); and Factor IX (Antihemophilic Factor B)].

In one embodiment, the mixture comprises a PCC concentrate (an acronym for: Prothrombinase Complex Concentrate referring to Factor II; Factor V; and Factor X).

In one embodiment, such liquid mixture is stable for at least 14 days at an ambient temperature selected from the group consisting of about 2, 3, 4, 5, 6, 7, and 8° C. In some embodiments, the liquid mixture remains stable for 30, 35, 45 days, 60 days, up to 90 days or more, at a temperature of about 2° C. to 8° C.

PPSB, a source of the vitamin K-dependent clotting zymogens, can be standardly produced as described in the art e.g. as described in "Production of plasma proteins for therapeutic use". Joseph Bertolini, Neil Goss, John Curling. 2013 Wiley Press. Concentrated PPSB can be produced by loading cryo-depleted human plasma on a DEAE anion exchange column and eluting with a concentrated salt solution (e.g. 0.25M NaCl) which also includes sodium citrate (NaCitrate e.g. 10 mM). The PPSB can be concentrated between 4-16 fold vs. plasma as determined by the prothrombin concentration (Factor II). Typically, the mixture comprises all of the vitamin K-dependent clotting zymogens that bind to anion exchange columns (such as FVII, FIX, protein C and protein S, and FX), their associated co-zymogens (FV and FVIII) and any other proteins that are co-eluted. The PPSB used to prepare the mixture can be further concentrated e.g. up to 50 fold vs. plasma.

Without being bound by theory, the vitamin K-dependent clotting zymogens small molecule inhibitors (e.g. NaCitrate, EDTA) serve to chelate calcium ions and prevent premature activation of any of the prothrombin complex comprising FII, FV, and FX, or any other $Ca^{2+}$ dependent process such as the Tenase complex activation (FVIII and FIX) or FXIII activation.

"Concentrated fibrinogen" relates to a fibrinogen concentration which is higher than the fibrinogen concentration in blood or plasma (greater than about 2-4 mg fibrinogen per ml and up to about 200 mg fibrinogen per ml). Concentrated fibrinogen includes, for example, fibrinogen at a concentration of about 20-40 mg/ml; about 15-40 mg/ml; about 10-200 mg/ml; 10-150 mg/ml; 20-150 mg/ml; about 30 mg/ml; or about 25-120 mg/ml. A concentrated fibrinogen may be prepared from any origin, for example, mammalian origin (e.g. from human blood plasma or pig plasma) or may be recombinant. In some embodiments, the concentrated fibrinogen is a cryoprecipitate. In some embodiments, the fibrinogen is plasma-supplemented e.g. the concentrated fibrinogen preparation and the plasma source are mixed in a ratio of about 3:1 to about 1:3 (w/v, v/v, or w/w), or about 2:1 to about 1:2 (w/v, v/v, or w/w), or about 1:1 (w/v, v/v, or w/w). A "plasma source" may be plasma from fractionation, pooled plasma, cryo-poor plasma, recovered plasma, and plasma which is the fluid portion of human blood collected by plasmapheresis. In one embodiment the plasma is thrombin depleted and/or factor depleted plasma.

In one embodiment, this mixture is stabilized by including small molecule inhibitors in the mixture such as, but not limited to, reversible serine protease active site inhibitors such as arginine, lysine, benzamidine or a combination thereof and/or a calcium chelator, for example, a citrate ion, oxalate ion e.g. at a concentration of 5 to 25 mM, EDTA, EGTA or a combination of such calcium chelators. In some embodiments, the calcium chelator is a citrate ion e.g. provided by sodium citrate. In some embodiments, the mixture comprises from about 1 mM to about 50 mM, or 5 mM to about 25 mM sodium citrate. In some embodiments, the mixture comprises from about 0.1 mM to about 2.5 mM EDTA and/or EGTA. In some embodiments, the mixture comprises from about 0.1% to about 5% (w/v) arginine. In some embodiments, the mixture comprises from about 0.1% to about 5% (w/v) lysine. In some embodiments, the mixture comprises from about 0.1 to about 10 mM benzamidine.

In some embodiments, the small molecule inhibitors in this mixture comprise 1-2 mM EDTA, 10 mM NaCitrate, and 1% (w/v) arginine-HCl.

In some embodiments, the resin bed is pre-equilibrated with 40-50 mM $CaCl_2$. Accordingly, in one embodiment, following passage of the mixture through the resin bed, the $CaCl_2$ concentration in the mixture is in the range of 35-45 mM, based on buffer exchange efficacy of at least 90%.

In another embodiment, following passage of the mixture through the resin bed, the inhibitor(s) concentration within the mixture is reduced to lower than 10% as compared to their initial concentration in the mixture, for example, lower than 0.1-0.2 mM EDTA, 1 mM NaCitrate, and 0.10% (w/v) arginine-HCl.

In one embodiment, the concentration of other small molecule reversible inhibitor(s) mentioned herein following passage of the mixture through the resin bed is reduced to lower than 10% as compared to their initial concentration in the mixture.

In some embodiments, the mixture comprises fibrinogen; vitamin K-dependent clotting zymogens comprising at least Factor II, Factor IX and Factor X; and at least one small molecule reversible inhibitor of at least one of the vitamin K-dependent clotting zymogen, wherein the mixture is free of added irreversible thrombin inhibitor.

In some embodiments, the mixture is free of calcium and comprises fibrinogen and Factor II and optionally Factor X.

The fibrinogen can be prepared from initial blood composition. The blood composition can be whole blood or blood fractions, i.e. a product of whole blood such as plasma. Fibrinogen can be autologous, human including pooled plasma, or of non-human source. It is also possible that the fibrinogen is prepared by recombinant methods or can be chemically modified.

In one embodiment of the invention, the fibrinogen solution is comprised from a biologically active component (BAC) which is a solution of proteins derived from blood plasma which can further comprise anti fibrinolytic agents such as tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which can be obtained from frozen plasma prepared from whole blood. A cryoprecipitate can be obtained when frozen plasma is thawed in the cold, typically at a temperature of 0-4° C., resulting in the formation of precipitate that contains fibrinogen and factor XIII. The precipitate can be collected, for example, by centrifugation and dissolved in a suitable buffer such as a buffer containing 120 mM sodium chloride, 10 mM trisodium citrate, 120 mM glycine, 95 mM arginine hydrochloride. The solution of BAC can comprise additional factors such as for example Factor VIII, fibronectin, von Willebrand factor (vWF), vitronectin, etc. for example, as described in U.S. Pat. No. 6,121,232 and WO9833533. The composition of BAC can comprise stabilizers such as tranexamic acid and arginine hydrochloride. The amount of tranexamic acid in the solution of BAC can be from about 80 to about 110 mg/ml.

In some embodiments, the cryoprecipitate is a Factor VIII-depleted cryoprecipitate.

In another embodiment, the concentration of plasminogen and plasmin in the BAC composition is lowered to equal or less than 15 µg/ml like for example 5 µg/ml or less plasminogen e.g. using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid or aprotinin.

The fibrinogen solution may be the BAC2 component (from EVICEL®) or any other fibrinogen containing solution, such as purified recombinant fibrinogen or cryoprecipitate produced from plasma.

In one embodiment, a mixture comprising the zymogens and fibrinogen is passed through a vessel that is packed with a porous resin. The zymogens and fibrinogen in the mixture will be too large to enter the pores of the resin and will quickly pass through the vessel. In contrast, the small molecules in the mixture e.g. the inhibitory small molecules will travel a more tortuous route, as they are able to enter and re-exit the pores of the resin, thus greatly slowing their rate of migration through the resin bed. The resin can also be pre-equilibrated with small molecule inducers such as phospholipids, cephalin and/or divalent cations (e.g. a calcium cation). Those inducers with which the resin has been pre-equilibrated enjoy an advantage of a significant "head-start", and therefore exit the resin together with the zymogens and fibrinogen.

In this embodiment, the term "inducer" refers to an agent that can initiate, facilitate and/or accelerate the conversion of a zymogen into an active enzyme. The term "inducer" herein is interchangeable with the terms "initiator" and "activator".

In one embodiment, the resin may include beads comprised of materials that known to activate the coagulation pathway e.g. silica and/or the resin beads may be covalently bound to molecules that may facilitate, accelerate and/or activate the coagulation pathway e.g. phospholipids. In one embodiment, the total volume of the aforementioned beads (out of the total resin bed volume) is up to 10% (v/v).

A second example relates to a mixture comprising fibrin monomers, dimers and/or oligomers and a reversible fibrin polymerization blocking agent (referred to herein as an "inhibitor") e.g. a GPR (SEQ ID NO: 1) peptide. In one embodiment, the pH of the mixture is neutral, for example, pH of about 6-8, or pH of about 6.5-7.5 or pH of about 6.7-7.2. The results show that a concentration of GPRP (SEQ ID NO: 1) peptide of greater than about 340 molar excess relative to the fibrin monomers and/or oligomers was efficient in (SEQ ID NO: 1) B preventing polymerization. Accordingly, in one embodiment, the GPRP (SEQ ID NO: 1) peptide is present in the mixture in an amount which is greater than about 340 molar excess relative to the fibrin monomers, dimers and/or oligomers.

In one embodiment, such a liquid mixture is stable for at least 14 days at an ambient temperature selected from the group consisting of about 20, 21, 22, 23, 24, and 25° C. Without wishing to be bound to theory, a GPRRP (SEQ ID NO: 1) peptide is capable of binding to a fibrin molecule, thereby blocking association and polymerization.

A reversible fibrin polymerization blocking agent can be an agent of less than about 1,000 daltons in size (a "small molecule as defined herein"). In some embodiments, the agent is an isolated peptide, a derivative or salt thereof, which is capable of reversibly binding a fibrin molecule and prevent or delay fibrin polymerization. In some embodiments, the reversible fibrin polymerization blocking agent comprises a small chemical molecule or an isolated peptide. Reversible fibrin polymerization blocking agent may be a low affinity binding agent to fibrin and having no permanent effects on fibrin polymerization. Therefore, typically passage of the mixture through the resin bed will result in reduction in the concentration of the agent/inhibitor, initiation and/or acceleration of polymerization and clot formation.

By "GPRP peptide" it is meant a peptide of four or more consecutive amino acid sequence set forth in SEQ ID NO: 1, specifically the sequence Gly-Pro-Arg-Pro. A GPRP peptide may comprise a tetramer (GPRP, SEQ ID NO: 1), a derivative or analog thereof. A GPRP (SEQ ID NO: 1) peptide may be 4 to 12 amino acid residues in length, or 4 to 8 preferably 4, 5, 6, 7 or 8 amino acids in length.

The amino acid sequences of GPRP (SEQ ID NO: 1) peptides may have one or more substitution, addition and/or deletion, including one or more non-naturally occurring amino acid. Preferably, derivatives exhibit at least about 50% identity to the reference sequence, preferably at least about 70% identity, more preferably at least about 75%, 80%, 85%, 90%, 91%, 92%, 93%, 94%, 95%, 96%, 97%, 98%, 99% or 100% sequence identity to the reference sequence described herein. Peptide derivatives can include modifications to the native sequence, such as deletions, additions and substitutions (generally conservative in nature), so long as the peptide maintains the desired activity e.g. reversibly inhibiting fibrin polymerization. In some embodiments, the GPRP (SEQ ID NO: 1) peptide includes a peptide, derivative or salt thereof comprising the Gly-Pro-Arg-Pro tetrapeptide amino acid sequence. In some embodiments, the GPRP peptide is a tetrapeptide having amino acid sequence set forth in SEQ ID NO: 1, or a derivative or salt thereof. In some embodiments, the GPRP peptide is a tetrapeptide consisting of an amino acid sequence set forth in SEQ ID NO: 1, or a derivative or salt thereof. In various embodiments, the term "GPRP peptide" includes a peptide selected from the group of peptides having an amino acid sequence selected from SEQ ID NO:1—SEQ ID NO:42 (SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO: 14; SEQ ID NO:15; SEQ ID NO: 16; SEQ ID NO: 17; SEQ ID NO: 18; SEQ ID NO: 19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40 SEQ ID NO:41; and SEQ ID NO:42) or derivative or salt thereof. In various embodiments, the GPRP peptide comprises an amino acid sequence as set forth in SEQ ID NO:1 to SEQ ID NO:42 or derivative or salt thereof. In various embodiments, the GPRP peptide is selected from the group of peptides having an amino acid sequence selected from SEQ ID NO:1 to SEQ ID NO:42 or derivative or salt thereof. In various embodiments, the GPRP peptide is selected from the group of peptides consisting of an amino acid sequence selected from SEQ ID NO:1 to SEQ ID NO:42 or derivative or salt thereof. In some embodiments, the GPRP peptide is a GPRP peptide amide. Any of the peptide sequences set forth in SEQ ID NOS: 1-42 may be a peptide amide. The amino acid sequences of any of the peptide sequences set forth in SEQ ID NOS: 1-42 may have one or more substitution, addition and/or deletion as defined above. Abbreviation, systematic names and formulae of common amino acids are known to the skilled in the art (Molecular Cell Biology edited by Darnell James E. Scientific American Books, Inc. 1986; page 54).

In some embodiments of this example, the mixture further comprises a thrombin-activated Factor XIII (Factor XIIIa). In such an embodiment, the mixture may further include a calcium chelator e.g. to prevent crosslinking of fibrin by Factor XIIIa which is dependent on the presence of calcium. The calcium chelator may be a citrate ion, oxalate ion e.g. at a concentration of 5 to 25 mM, EDTA, EGTA or a combination of such calcium chelators. In various embodiments, the calcium chelator is a citrate ion provided, for example, as sodium citrate. In some embodiments, the mixture comprises from about 1 mM to about 50 mM sodium citrate. In some embodiments, the mixture comprises about 0.1 to about 2.5 mM EDTA and/or EGTA.

In some embodiment, a mixture comprising the fibrin monomers, dimers and/or oligomers and a GPRP (SEQ ID NO: 1) peptide is passed through a vessel that is packed with the porous resin. The fibrin molecules in the mixture will be too large to enter the pores of the resin and will quickly pass through the resin bed and exit the device. In contrast, the small inhibitory molecules e.g. GPRP (SEQ ID NO: 1) peptide in the mixture will travel a more tortuous route, as they are able to enter and re-exit the pores of the resin, thus greatly slowing their rate of migration through the resin bed.

In one embodiment, the concentration of the agent/inhibitor after passage through the device is controlled by pre-equilibrating the resin bed with the desired final concentration of the agent, e.g. GPRP (SEQ ID NO: 1) peptide. Without being bound by the mechanism, by including a fixed concentration of the agent within the resin bed one can control the fibrin polymerization or fibrin clot formation rate.

Monomeric, dimeric and/or oligomeric fibrin may be obtained by contacting an aqueous fibrinogen comprising solution e.g. as the one described above with thrombin and/or thrombin-like enzyme under conditions that allow cleavage of fibrinogen to fibrin. Examples of such an enzyme are snake venom enzymes that cleave fibrinopeptide A (FpA) like Batroxobin. In such an embodiment, preparation of fibrin is carried out under conditions that fibrin polymerization is inhibited e.g. in the presence of GPRP (SEQ ID NO: 1) other reversible fibrin polymerization blocking agent. In another embodiment, fibrin is obtained from fibrinogen under conditions which inhibit polymerization (e.g. by lowering temperature) and GPRP (SEQ ID NO: 1) peptide is added later on. The thrombin may be free in solution or immobilized on beads. If thrombin is immobilized on beads, for example, beads in batch form or in a column and the fibrinogen solution is passed through/contacted with the beads, the resulting mixture may comprise residual amounts of thrombin. In some embodiments, the mixture is substantially free of thrombin, for example, has less than about one (1) IU/ml of thrombin. In one embodiment, the thrombin used to obtain fibrin is a sterile solution, pH 6.8-7.2, which contains highly purified human thrombin. Thrombin is a highly specific protease that transforms the fibrinogen into fibrin. The thrombin solution can contain: human thrombin (800-1200 IU/ml), calcium chloride, human albumin, mannitol, sodium acetate and water for injection. In one embodiment, thrombin is manufactured by chromatographic purification of prothrombin from cryopoor plasma followed by activation with calcium chloride e.g. as described in U.S. Pat. No. 5,143,838, which is incorporated herein by reference.

The fibrinogen and thrombin components used according to the invention can be part of a two liquid fibrin sealant component. The components can be prepared from plasma of human beings or mammals. However, it is also possible that the components are prepared by recombinant methods.

In one embodiment, the mixture further comprises arginine e.g. Arginine-HCl at a concentration of up to 4% (w/v).

In some embodiments, the liquid mixture comprises fibrin at a concentration of 1 to 13% (w/v) and a GPRP (SEQ ID NO: 1) peptide or other reversible fibrin polymerization blocking agent; wherein the blocking agent or GPRP (SEQ ID NO: 1) is present in the mixture in an amount which is greater than 100 fold molar excess relative to the fibrin. In various embodiments, the fibrin is present in the mixture at a concentration of 1 to 13% (w/v). In various embodiments, the fibrin is present in the mixture at a concentration of 1 to 4% (w/v) or 3.5 to 13% (w/v).

In some embodiments, the GPRP (SEQ ID NO: 1) peptide is present in an amount greater than about 340 fold molar excess relative to the fibrin.

In some embodiments, the GPRP (SEQ ID NO: 1) peptide is present in an amount of about 340 to 460 fold molar excess relative to the fibrin. In some embodiments, the mixture is substantially free of added thrombin.

In one embodiment, passage of the mixture through the resin bed reduces the concentration of the fibrin polymerization blocking agent e.g. GPRP (SEQ ID NO: 1) with respect to the fibrin and is in a ratio of equal to or lower than 340.

In one embodiment, passage of the mixture through the resin bed reduces the concentration of the fibrin polymerization blocking agent e.g. GPRP (SEQ ID NO: 1) with respect to the fibrin and is in a ratio of equal to or lower than 100 such as in the ratio of 1-60, for example 3, 4, 11, 11.3, 17, 22.7, 23, 34, 45, 56.7, or 57.

Following contact of the mixture with the resin bed the GPRP (SEQ ID NO: 1) concentration can be reduced according to an intended use. Typically, for hemostasis it will be of advantage to obtain clotting times which are less than one minute. In one embodiment, passage of the mixture through the resin bed reduces the GPRP (SEQ ID NO: 1) concentration in the mixture to a molar excess of equal to or less than 100 fold or to a molar excess of equal to or less than 34 fold relative to the fibrin.

For graft fixation it will be of advantage to obtain clotting times which are approximately 15 minutes. In one embodiment, the GPRP (SEQ ID NO: 1) concentration in the mixture is reduced to a molar excess of equal to or less than 100 fold or to a molar excess of equal to or less than 56 fold relative to the fibrin.

Other removal or dilution options include addition of GPRP (SEQ ID NO: 1) complimentary moieties to the resin bed. Complimentary moieties in the resin bed would be essentially an affinity method.

Alternatively or in addition, the GPRP (SEQ ID NO: 1) in the mixture could be neutralized and/or blocked by adding a peptide e.g. a complementary moiety of a GPRP peptide or an antibody capable of displacing GPRP bound to the fibrin.

A third example relates to a mixture comprising fibrin monomers, dimers and/or oligomers in acid media e.g. as described in U.S. Pat. No. 8,367,802.

In such an embodiment where the mixture is stabilized by a low pH, the inhibitory small molecules are, for example, hydronium ion ($H_3O$). The concentration of the small molecule can be reduced as described above by using the device/system according to the invention. Alternatively or additionally, the concentration of hydroxyl ion (OH—) may be increased to neutralize the acidic hydronium ions by using the device/system according to the invention.

Figure 3:
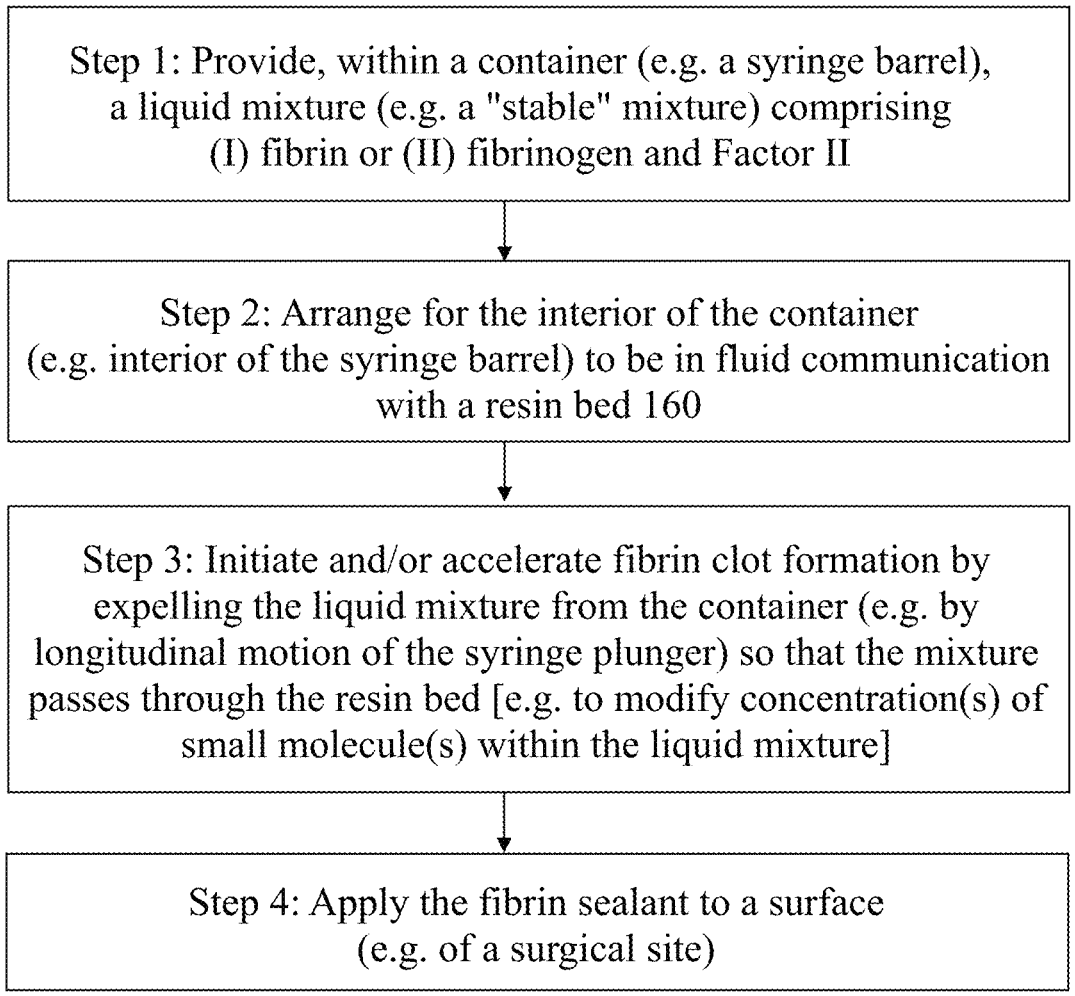
FIG. 3 is a flow-chart of an embodiment method for preparing and delivering fibrin sealant to a surface by using a device according to the invention.

FIG. 3 is a flow-chart of an exemplary method for preparing and delivering fibrin sealant to a surface by using a device according to the invention, the device comprising a mixture (for example, a stable mixture and/or a mixture comprising (i) fibrin monomers, dimers and/or oligomers or (ii) fibrinogen and Factor II).

A "surface" is a position or location where one desires to form the clot. The surface depends on the use of the sealant. The fibrin sealant may be used, for example, in hemostasis, tissue fixation, graft fixation, wound healing and anastomosis. The surface can be an injured surface. The surface can be a bleeding or non-bleeding site in a subject. The surface can also be a working surface outside the body. The devices, systems, methods, and kits disclosed herein can be used internally and externally, for delivering a fibrin sealant for tissue and organ graft fixation, for sealing a surgical wound, in vascular surgery including providing hemostasis and for anastomoses such as arterial, gastrointestinal and tracheal anastomoses.

The surface can be an external surface of the skin that can be seen by unaided vision and a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; and the cardiac muscle.

The kit can be provided as separated elements which can be assembled to form a device/kit according to the invention. In one embodiment, the resin is provided separately, and is then packed within a vessel and/or equilibrated according to the requirements as dictated by the composition of the liquid mixture used.

For assembly of the device, the resin beads can be provided as wet pre-equilibrated particles or as dry particles. In the latter embodiment, the kit comprises an equilibration buffer, and the resin bed can be equilibrated with 3 to 6 (e.g. 5) resin bed volumes of a buffer by passing the buffer through the device.

In one embodiment, the fibrin mixture, the fibrinogen and Factor II mixture and/or the liquid phase of the resin bed are provided in solid form and are reconstituted in an aqueous solution prior to assembly of the device/system. Accordingly, the kit may comprise at least one container with an aqueous solution for reconstitution. Suitable containers include, for example, ampoules, vials, syringes and test tubes. The containers can be made of, for example, glass, metal or plastic. The kit may include instructions for use.

Reconstitution of the fibrin mixture or the fibrinogen and Factor II mixture can be carried out by the addition of various volumes of a pharmaceutically acceptable carrier. Reconstitution of the liquid phase of the resin bed can be carried out in a liquid solution comprising the small molecule solutes as described herein.

The term "reconstitution" refers to a process in which solid is converted into a liquid form. A reconstituted product can be a liquid product made by adding aqueous liquid to dry solids from which the liquid has been previously removed.

Alternatively, the fibrin mixture, the fibrinogen and Factor II mixture and/or the liquid phase of the resin bed can be provided in frozen form, e.g. at a temperature of −18° C. or lower, and thawed prior to assembly of the device/system.

The term a "pharmaceutically acceptable carrier" refers to any diluent or a vehicle which is suitable for human or other animal use. The carrier can be selected from any of the carriers known in the art such as, but not limited to, phosphate buffered solution (PBS), saline, sodium chloride solution, calcium chloride solution, lactated ringers (LR), 5% dextrose in normal saline, and water for injection.

In one embodiment, the method comprises a step of passing the mixture 190 through resin bed 160. In Step 1, the liquid mixture is provided within a container (e.g. a syringe barrel 124)—for example, as a stable mixture. In Step 2, an interior of the container (e.g. 124) is arranged to be in fluid communication with an interior of vessel 158 and/or in communication with resin bed 160.

In one non-limiting example, a proximal and female port of vessel 158 is covered or sealed and in Step 2, (i) this covering or seal is removed and (ii) distal tip 126 of syringe barrel 124 is inserted into the proximal and female port e.g. socket 128 so that respective interiors syringe barrel 124 and vessel 158 are brought into fluid communication with each other. For example, syringe barrel 124 and vessel 158 may be attachable (e.g. detachably attachable) to each other, and may be attached to each other in Step 2. In Step 3, the liquid mixture is expelled from the container (e.g. syringe barrel) and forced to flow through resin bed 160. Passage through resin bed 160 results in fibrin clot formation with a clotting time ($T_{CLOT}$) of at most 1 hour at an ambient temperature selected from the group consisting of 21° C., 22° C., 23° C., 24° C., and 25° C.

After passing through resin bed (e.g. to exit vessel 158) via a distal port 194 thereof, the fibrin sealant may be applied to a surface—e.g. to a surface of a surgical site —Step 4.

Distal port 194 may be attached to an application tip through which the fibrin sealant may be conveyed to the surface.

The device according to the invention can be used to pass a mixture a second time, after its washing with a suitable pre-equilibration buffer (e.g. according to the mixture to be applied).

In some embodiments, the container e.g. syringe barrel 124 and/or vessel 158 can be of variable dimensions so as to enable variable amounts, and relations of mixture:resin ratios.

In some embodiments, for significant buffer exchange which is translated to the removal of the majority of small molecules and their replacement with other small molecules, the packed resin bed is comprised of approximately 60-70% (v/v) solid material, and the remaining 30-40% (v/v) is comprised of a liquid solution which contains the small molecule solutes. In some embodiments, the volume of the liquid mixture, prior to the passage through the resin bed, is substantially equal to the volume of the liquid phase of the resin bed. Typically, the small molecules are displaced and exchanged when a volume of liquid mixture 190 comprising proteins is driven through the device as described. Thus, the protein solution is exuded from the device having a substantially similar volume as before passage through resin bed 160 and with minor to no changes in protein composition, whereas the solutes/small molecules are exchanged as they are passed through the resin.

In some embodiments, the resin is pre-equilibrated with a buffer solution. This buffer solution may be of such a nature as to support enabling activation of zymogens e.g. Factor II, such as in mixtures comprising vitamin K-dependent clotting zymogens and fibrinogen, to bring about thrombin generation. In one embodiment, the buffer within the vessel 158 comprises calcium ions such as provided by calcium chloride at a concentration range of about 8-30 mM; phospholipids; cephalin; and combinations thereof.

In one embodiment, the resin include beads comprised of materials that known to activate the coagulation pathway e.g. silica and/or the resin beads are covalently bound to molecules that may facilitate, accelerate and/or activate the coagulation pathway e.g. phospholipids. In one embodiment, the total fraction of the aforementioned beads is up to 10% (v/v).

In another embodiment, the device is used with a mixture 190 containing monomeric, dimeric and/or oligomeric fibrin stabilized with an inhibitory fibrin polymerization blocking agent. In one embodiment, the equilibration buffer within the device comprises $CaCl_2$, arginine, and fixed concentrations of inhibitory agent e.g. GPRP (SEQ ID NO: 1), salts or derivatives thereof at a concentration in the range of 0-20 mM, or 0.1-5 mM, or 1-3 mM. Typically, "gel filtration" or "buffer exchange" is a mode of chromatography where the solid phase (the resin in the device) is highly porous. The larger molecules, such as proteins, are too large to be caught within the pores. Small molecule inhibitors, on the other hand, are greatly delayed as a consequence, and are effectively replaced by the small molecules (e.g. calcium ions) with which the resin had been pre-equilibrated. Significantly, while protein components may be added to the device and will be rapidly exuded from the device, proteins are typically not subtracted from the mixture by this mean. In one embodiment, the use of this device allows for the application of a mixture comprising highly concentrated fibrinogen, associated proteins. In one embodiment, the mixture comprises plasma proteins such as Factor XIII, Factor VIII, fibronectin, vitronectin, and others.

All numerical values are intended to include +/−10%.

When a numerical value is preceded by the term "about", the term "about" is intended to indicate +/−10%.

Several embodiments of the device are described.

EXAMPLES

In examples 1 and 2, a commercial gel filtration spin column (Disposable PD-10 Desalting Columns, Product code: 17-0851-01, GE Healthcare, Sweden) was utilized to prove the concept of using buffer exchange to remove small molecule inhibitor(s) and/or add small molecule activator(s) to a single component fibrin sealant liquid mixture in order to generate a fibrin sealant therefrom. This column was used as it is guaranteed by the manufacturer to be a high efficiency column for exchanging small molecules without loss of proteins (>90% small molecule exchange). Typically, when a mixture is passed through a pre-equilibrated desalting column an efficient buffer exchange will result in an eluent mixture (e.g. the mixture obtained following passage through the column) comprising a concentration of at least 90% of the pre-equilibration buffer and/or in a reduction in the concentration of small molecules inhibitors within the mixture to lower than 10% as compared to their initial concentration within the mixture.

This column and other known columns, however, are long and narrow (in this case, the height:width ratio is >3). In order to pass the mixture through the column, either a long processing time (when utilizing gravity) or significant force (e.g. using a centrifuge) is required. These columns are typically not compatible with hand-held devices (e.g. a syringe). Without being bound to the mechanism, the device of the invention comprises a resin bed that is geometrically distributed so that it can be manipulated by the force applied by a human thumb muscle power and yet provide an efficient buffer exchange.

When using the commercial column in the experiments below, 2.5 ml liquid mixture was passed. The commercial column was prepared and equilibrated according to the manufacturer's instructions. The volume of the resin bed (as given by the manufacturer) was 8.3 ml (referred herein as "resin bed"). The liquid mixture volume was 30.1% of the resin bed volume.

The resin used in the Disposable PD-10 Desalting Columns was identical to Sephadex G-25 Medium (Product code: 17-0033-01; GE Healthcare, Sweden) with the following characteristics: Matrix: Cross-linked dextran; Separation mechanism: According to size; Wet particle size range: 38 to 235 µm; Dry particle size: >50 µm; Exclusion limit (Mr): 5000; Chemical stability: All commonly used buffers; Working pH range: 2 to 13.

In all Examples below, the mixture was at a temperature range of 22-37° C. and at a pH in of about 7.0 while passing through the resin bed.

Example 1: Fibrin Clot Formation from a Liquid Mixture Comprising Fibrinogen and Factor II Using a Gel Filtration Column The following example aims to show that initiation and/or acceleration of fibrin clot formation can be achieved by modifying the concentrations of small molecule(s). For this purpose, a 5-fold concentrated extract of vitamin K-dependent clotting zymogens as determined by the prothrombin concentration (Factor II) (compared to plasma) was prepared as described in the art (Production of plasma proteins for therapeutic use. Joseph Bertolini, Neil Goss, John Curling. 2013 Wiley Press). This extract (PPSB concentrate) contained Factor II, VII, IX and X as well as the cofactor Factor V and additional proteins that co-elute using this method.

Briefly, concentrated PPSB, was produced by loading cryo-depleted human plasma on a DEAE anion exchange column and eluting with a concentrated salt solution (0.25M NaCl) which also includes 10 mM sodium citrate (NaCitrate). The PPSB was concentrated between 4-16 fold vs. plasma as determined by the prothrombin concentration (Factor II).

The mixture comprised all of the vitamin K-dependent clotting zymogens that typically bind to anion exchange columns (such as FVII, FIX, protein C and protein S, and FX), their associated co-zymogens (FV and FVIII) and any other proteins that are co-eluted.

The vitamin K-dependent clotting zymogens inhibitors (e.g. NaCitrate, EDTA) served to chelate calcium ions and prevent premature activation of any of the prothrombin complex comprising FII, FV, and FX, or any other $Ca^{2+}$ dependent process such as the Tenase complex activation (FVIII and FIX) or FXIII activation.

This extract was mixed with a concentrated fibrinogen solution (BAC2 component; a fibrinogen comprising component from EVICEL® Fibrin Sealant) at a one to one volumetric ratio, finally yielding approximately 3.5% (w/v) fibrinogen, and approximately 0.14 international units (IU) of Factor II per mg of fibrinogen. Small molecule inhibitors included in this mixture were: 1-2 mM of EDTA, 10 mM NaCitrate, and 1% (w/v) arginine-HCl.

To efficiently remove these small molecule inhibitors and add a calcium ion inducer, a commercially available buffer exchange spin column (Disposable PD-10 Desalting Columns, Product code: 17-0851-01, GE Healthcare) that has been characterized to efficiently replace 90% of small molecule (buffer) components in selected protein mixtures, was used. The column was pre-equilibrated with either $CaCl_2$) (40-50 mM), or a buffer solution without calcium.

The mixture was subjected to the buffer exchange procedure as per manufacturer's instructions. Clotting was assessed by inverting the tube containing the buffer-exchanged extract.

Figure 4A:
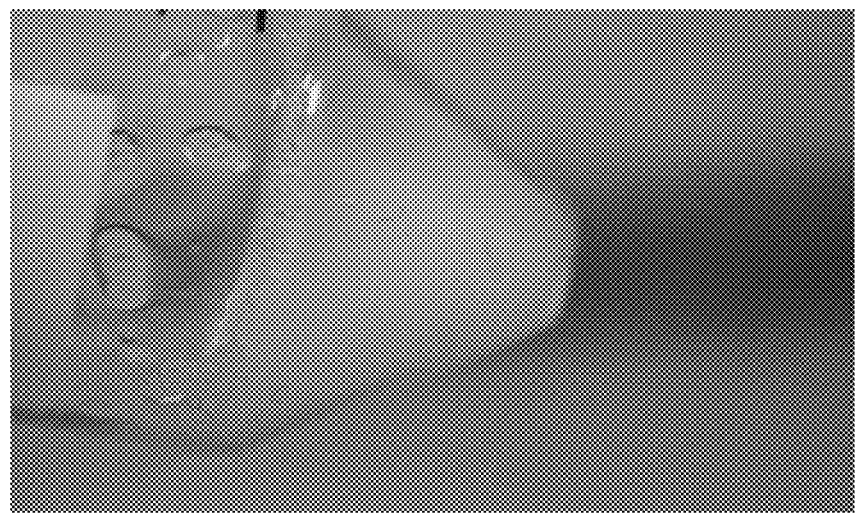
FIG. 4A shows a liquid mixture subjected to small molecule exchange by passing the mixture through a commercial column (Disposable PD-10 Desalting Column) pre-equilibrated with $CaCl_2$. Following the exchange, a fibrin clot was spontaneously formed.
Figure 4B:
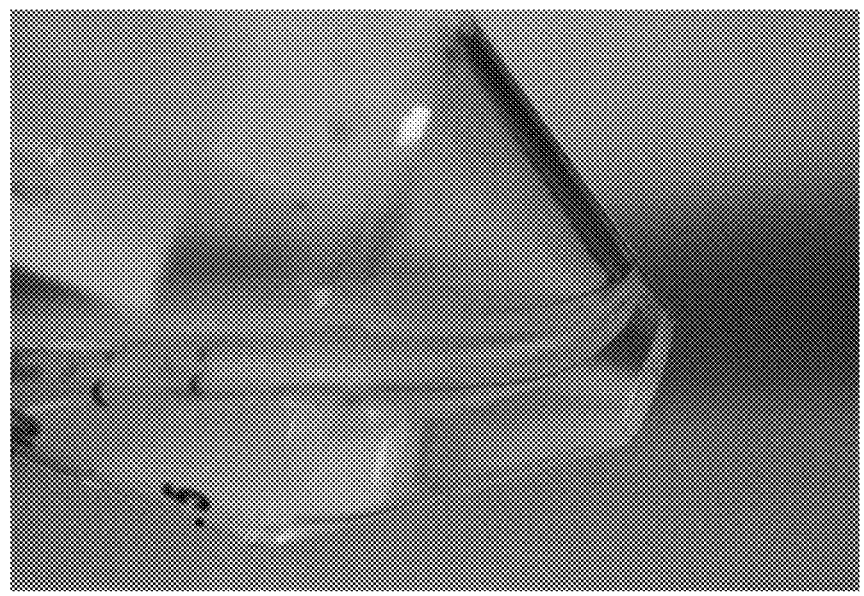
FIG. 4B shows a liquid mixture subjected to small molecule exchange by passing the mixture through a commercial column pre-equilibrated with a buffer lacking $CaCl_2$. No clotting occurred even after several days.

The results show that a mixture which passed through the column pre-equilibrated with $CaCl_2$ clotted spontaneously (FIG. 4A) within less than 30 minutes, whereas the solution which passed through the buffer lacking $CaCl_2$ did not clot, even after several days (FIG. 4B).

Fibrin clot formation was also tested by adding $CaCl_2$ directly into the same mixture in a test tube, without removal of the small molecule inhibitors and without using the buffer exchange technique. The time to clot was above 120 minutes.

This experiment shows that using a buffer exchange technique in a dedicated device could be used to initiate and/or accelerate fibrin clot formation from a stable liquid mixture.

Example 2: Fibrin Clot Formation from a Liquid Mixture Comprising Fibrin and GPRP (SEQ ID NO: 1) Using a Gel Filtration Column The following example aims to show that initiation and/or acceleration of fibrin clot formation can be achieved by removing a small molecule inhibitor.

Fibrin monomers, dimers and/or oligomers were generated in the following manner:

First, a mixture of 3.5% (w/v) fibrinogen and 40 mM GPRP (SEQ ID NO: 1) [a large molar excess relative to fibrinogen (>350)] was prepared. This molar ratio was found to be sufficient to maintain the mixture stable.

GPRP (SEQ ID NO: 1) (Gly-Pro-Arg-Pro; custom made by Sigma; the peptide was supplied in lyophilized form (250 mg) and dissolved in 100 mM tri-Sodium Citrate dihydrate; pH=7 creating 1 M GPRP).

Thrombin (as in EVICEL® Fibrin Sealant) was next added to generate fibrin from fibrinogen (to a final concentration of 10 IU/ml or 100 IU/ml), in the presence of the GPRP (SEQ ID NO: 1). The commercial column (PD-10) used in Example 1 was also used to remove the GPRP (SEQ ID NO: 1) peptide. The column was pre-equilibrated with a buffer including 20 mM sodium acetate pH 7.0; 25 mM calcium chloride.

The fibrin concentration was estimated as being equal to the fibrinogen concentration.

2.5 ml liquid mixture was subjected to the buffer exchange procedure and the fibrin clot formation was assessed by inverting the tube containing the buffer-exchanged mixture.

The remaining liquid mixture was maintained at an ambient room temperature (about 22-24° C.) for a period of 24 hours to assess whether a clot could be formed without removal of the GPRP (SEQ ID NO: 1).

Figure 5A:
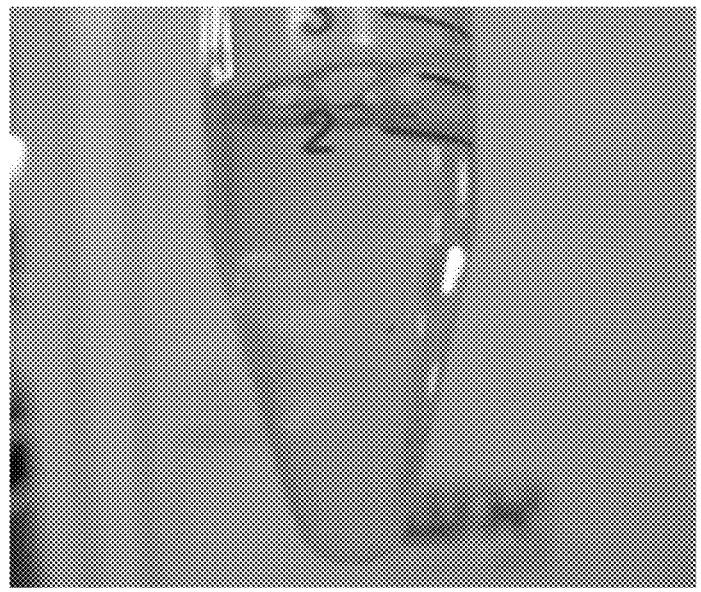
FIG. 5A shows that a GPRP (SEQ ID NO: 1) —inhibited fibrin solution, which was not subjected to the buffer exchange procedure, remained in liquid form for the tested time period under the tested conditions [at an ambient room temperature (about 22-24° C.) for a period of 24 hours].
Figure 5B:
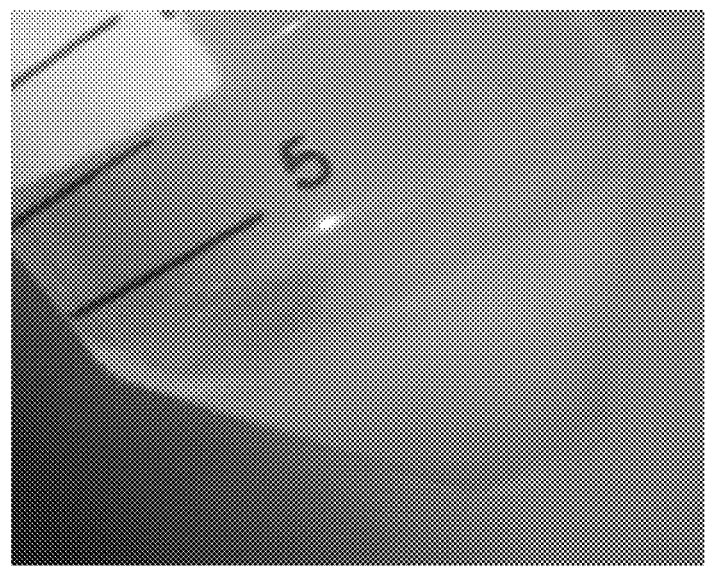
FIG. 5B shows the polymerized liquid mixture after removal of the GPRP (SEQ ID NO: 1)-inhibitor by a buffer exchange procedure using a column.

FIG. 5A shows that the GPRP (SEQ ID NO: 1) inhibited fibrin solution, which was not subjected to the buffer exchange procedure, remained in liquid form for the tested time period under the tested conditions. FIG. 5B shows the polymerized mixture after passage through the column and removal of the GPRP (SEQ ID NO: 1) inhibitor.

This experiment shows that using a buffer exchange technique in a dedicated device could also be used to initiate and/or accelerate fibrin clot formation by removal of an inhibitor.

Example 3: The Effect of Passing a Liquid Mixture Comprising Fibrinogen and Factor II Through a Device According to the Invention In this example, the efficiency of the device of the invention in modifying the concentration of small molecules in the mixture was compared to the commercial column which is known to be >90% efficient and was shown in Example 1 and 2 to be efficient in fibrin clot formation.

To this end, a commercial GE PD-10 buffer exchange column was compared to two embodiments of the device according to the invention utilizing the same buffer exchange resin as the commercial column (Sephadex G25 Medium; Product code: 17-0033-01; GE Healthcare, Sweden) and having the following resin bed geometries:
1. 25 mm diameter (width), 13 mm height (6.4 ml resin bed volume) —a height to width ratio of 0.52.
2. 25 mm diameter (width), 25 mm height (12.3 ml resin bed volume) —a height to width ratio of 1.

A device as shown in FIG. 1 was assembled with two different vessel 158 sizes suitable to accommodate the above resin bed volumes. Filters 150, 170 were Watmann papers flanked at each side with a Support Screen for Columns, i.d. 26 mm; Product code: 18-9377-01; GE Healthcare, Sweden). One Support Screen was located proximal to filter paper 150; the other was located distal to filter paper 170.

A 10 ml typical syringe 120 was used. The commercial column was prepared and equilibrated according to the manufacturer's instructions.

The resin bed was equilibrated with 5 resin bed volumes of a buffer containing 50 mM $CaCl_2$, 20 mM NaAcetate, pH 7.0 by passing the buffer through the device 5 times.

A mixture containing 2.5-fold concentrated zymogen extract, compared to plasma, and 3.5% (w/v) fibrinogen [prepared by mixing a 5-fold concentrated zymogen extract with a concentrated fibrinogen solution (EVICEL® BAC2 component) at a one to one volumetric ratio] was passed through the column (2.5 ml) and through the devices (2 ml, or 4 ml) to exchange the buffer to initiate fibrin clot formation.

The mixture volumes used were equal to 30-35% of the resin bed volume. Fibrin clot formation was assessed by cessation of flow of the mixture.

The time to fibrin clot formation was 25-30 minutes for the column and the devices.

When the device according to the invention was used to passage the mixture a second time, after washing with the pre-equilibration buffer, a reduction in the time to form a fibrin clot was observed. Without being bound to theory, the passage of liquid through the resin bed results in its compression.

Table 1 shows the time to fibrin clot formation after using the devices according to the invention and a commercial column.

TABLE 1

The time to fibrin clot formation after using the devices according to the invention and a commercial column.

| | Time to fibrin clot formation (minutes) |
|---|---|
| PD-10 commercial column | 25 |
| Device I according to the invention (6.4 ml resin bed volume) | 30 |
| Device II according to the invention (12.3 ml resin bed volume) | 26 |
| Device I, $2^{nd}$ pass | 24 |
| Device II, $2^{nd}$ pass | 23 |

The results above show that the efficiency of the device of the invention is equivalent to the efficiency of the tested commercial column. In addition, the results show that the compression of the resin bed affects the time to fibrin clot formation.

Example 4: The Effect of Calcium Ion Inducer Concentration on the Rate of Fibrin Clot Formation In the following experiment, the concentration range of calcium ion ($CaCl_2$ concentration) as an inducer to accelerate fibrin clot formation in the zymogen (PPSB concentrate) and fibrinogen comprising mixture (prepared from BAC2) described in Example 1 was explored. In this Example, the zymogen mixture was prepared at a concentration of 10-fold (10 IU FII/ml), as compared to plasma, and mixed in the same volumetric ratio with the same fibrinogen solution as above (final 5-fold concentrations of zymogen, compared to plasma, and 3.5% (w/v) fibrinogen). No EDTA was used. In this experiment, initiation of clotting was performed using a calcium-depleted PT (prothrombin time) reagent comprising tissue factor and phospholipids; a clotting initiator that is typically present in bleeding/injured surfaces and on the surface of activated platelets, respectively. By using both tissue factor and phospholipids, a bleeding surface is simulated. $CaCl_2$ at increasing concentrations was supplemented to the mixture and the clotting time was measured using a Start4 clotting analyzer (Diagnostica Stago).

Figure 6:
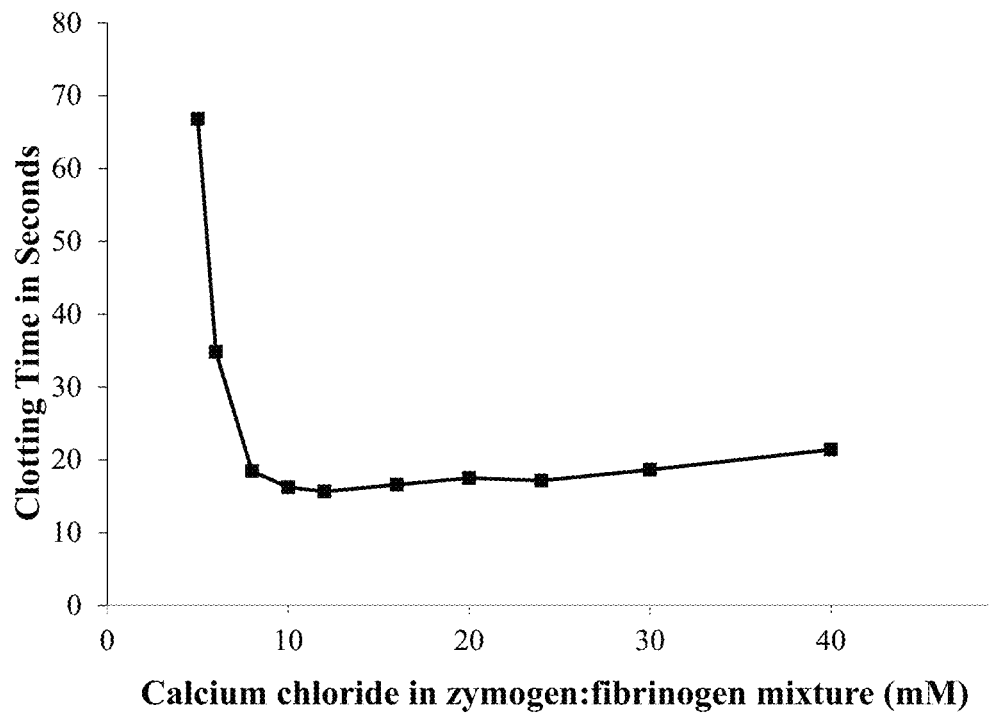
FIG. 6 shows rapid clotting of a zymogen:fibrinogen mixture supplemented with tissue factor and phospholipids is dependent on the $CaCl_2$ concentration.

FIG. 6 shows rapid clotting (<20 seconds) was obtained at $CaCl_2$ concentration of between about 8 mM to about 30 mM. Within the allotted parameters (maximal time allowed for clot measurement—999 seconds), no clotting was observed with no calcium addition.

These results show that advantageously increasing the concentration of the calcium ion within the mixture accelerates the rate in which clotting occurs.

The results also show that pre-equilibrating the resin bed with set calcium ion concentrations can be utilized as a method to control the rate of fibrin clot formation.

Example 5: Controlling the Rate of Fibrin Clot Formation by Adjusting the Small Molecule GPRP (SEQ ID NO: 1) Inhibitor Concentration within the Mixture In the following experiment, the effect of adjusting the concentration of GPRP (SEQ ID NO: 1) inhibitor on fibrin clot formation rate was tested. GPRP (SEQ ID NO: 1) at different concentrations (0.1 mM, 0.2 mM, 0.5 mM, 1 mM, 1.5 mM, 2 mM, 3 mM, 4 mM, and 5 mM) was added to a fibrinogen containing solution (a fixed concentration of 3% w/v, prepared by diluting the BAC2 component of EVICEL® in 40 mM citrate buffer).

All of these (having a ratio of at most about 57:1) are below the minimal ratio required for long term stabilization (e.g. for at least 14 days at an ambient temperature selected from the group consisting of about 20, 21, 22, 23, 24, and 25° C.) of fibrin monomers. It was shown that to obtain a long term stabilization GPRP (SEQ ID NO: 1) is present in the mixture in an amount which is greater than 100 fold molar excess relative to the fibrin monomers e.g. greater than about 340 fold or about 340 to 460 fold molar excess relative to the fibrin monomers.

To generate fibrin monomers, dimers and/or oligomers, thrombin was added to the mixture; a 10% volume of the thrombin component of EVICEL® was added to yield a final concentration of 100 international units/ml (IU/ml). The rate of fibrin clot formation was measured by cessation of flow of the mixture upon inversion of the tube. The results are shown in Table 2.

TABLE 2

The GPRP (SEQ ID NO: 1) concentrations in the mixture relative to fibrin and polymerization time (time to clot) of the mixture. 3% fibrin

| GPRP concentration | Time to clot | Fold (GPRP:fibrin) |
|---|---|---|
| 0.1 mM | 5 seconds | 1.1 |
| 0.2 mM | 7 seconds | 2.3 |
| 0.5 mM | 11 seconds | 5.7 |
| 1 mM | 13 seconds | 11.3 |
| 1.5 mM | 22 seconds | 17 |
| 2 mM | 28 seconds | 22.7 |
| 3 mM | 2.5 minutes | 34 |
| 4 mM | 8 minutes | 45 |
| 5 mM | 15 minutes | 56.7 |

Figure 7:
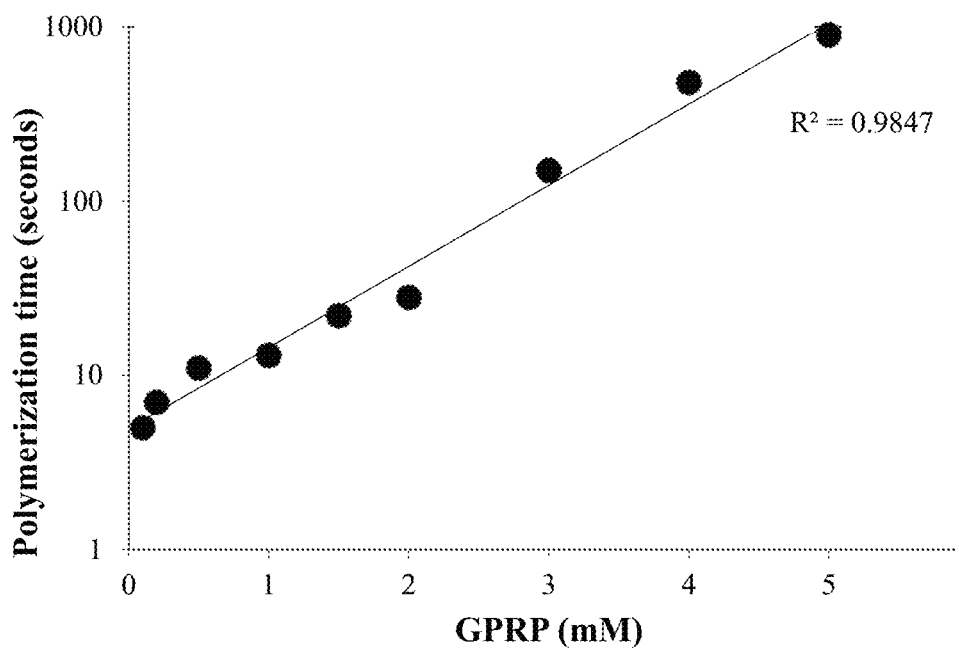
FIG. 7 shows that there exists a logarithmic correlation between the rate of fibrin polymerization and the concentration of GPRP (SEQ ID NO: 1) peptide comprising an amino acid sequence set forth in SEO ID NO.

FIG. 7 shows that there exists a logarithmic correlation between the rate of fibrin polymerization and the concentration of GPRP (SEQ ID NO: 1). Above a molar ratio of 340:1 GPRP (SEQ ID NO: 1): fibrin, no polymerization was observed for >14 days (in the tested fibrinogen concentration—40 mM GPRP).

The results indicate that pre-equilibrating the resin bed with set GPRP (SEQ ID NO: 1) centrations can be utilized as a method to control the rate of fibrin clot formation.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to. The term "including" is used herein to mean, and is used interchangeably with, the phrase "including but not limited to". The term "or" is used herein to mean, and is used interchangeably with, the term "and/or", unless context clearly indicates otherwise. The term "such as" is used herein to mean, and is used interchangeably with, the phrase "such as but not limited to". As used herein, the terms "comprising", "including", "containing", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

The invention claimed is:

1. A method for preparing and delivering a fibrin sealant to a surface, the method comprising:
   a. providing a quantity of a cell-free liquid mixture comprising:
      I. fibrin or
      II. fibrinogen and Factor II; and
   b. passing the mixture through a resin bed comprising a size-exclusion chromatographic resin pre-equilibrated with calcium so as to (i) reduce a concentration of a small molecule inhibitor(s) of fibrin clot formation within the mixture and/or (ii) increase a concentration of the calcium within the mixture, so that after the passage of the mixture through the resin, a fibrin clot is formed with a clotting time ($T_{CLOT}$) of at most 1 hour at an ambient temperature selected from the group consisting of 21° C., 22° C., 23° C., 24° C., and 25° C.

* * * * *